US012797151B2

(12) United States Patent
Hannaford et al.

(10) Patent No.: US 12,797,151 B2
(45) **Date of Patent: *Nov. 17, 2026**

(54) SYSTEMS AND METHODS FOR BIFURCATED NAVIGATION CONTROL OF A MANIPULATOR CART INCLUDED WITHIN A COMPUTER-ASSISTED MEDICAL SYSTEM

(71) Applicant: Intuitive Surgical Operations, Inc., Sunnyvale, CA (US)

(72) Inventors: Sophia R. Hannaford, Seattle, WA (US); Marisa C. Babb, Santa Clara, CA (US); Simon P. DiMaio, San Carlos, CA (US); Craig Gotsill, San Francisco, CA (US); Brandon D. Itkowitz, San Jose, CA (US); Omid Mohareri, San Francisco, CA (US); Dinesh Rabindran, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 29 days.

This patent is subject to a terminal disclaimer.

(21) Appl. No.: 19/000,109

(22) Filed: Dec. 23, 2024

(65) Prior Publication Data

US 2025/0127586 A1 Apr. 24, 2025

Related U.S. Application Data

(63) Continuation of application No. 17/610,376, filed as application No. PCT/US2020/035237 on May 29, 2020, now Pat. No. 12,213,814.

(Continued)

(51) Int. Cl.
*A61B 50/13* (2016.01)
*G05D 1/622* (2024.01)
*G05D 1/82* (2024.01)

(52) U.S. Cl.
CPC ............ *A61B 50/13* (2016.02); *G05D 1/622* (2024.01); *G05D 1/82* (2024.01)

(58) Field of Classification Search
CPC ........ A61B 50/13; A61B 34/00; G05D 1/622; G05D 1/82; B25J 9/162; B25J 9/1676
See application file for complete search history.

(56) References Cited

U.S. PATENT DOCUMENTS

| | | | | |
|---|---|---|---|---|
| 2014/0067121 A1* | 3/2014 | Brooks | B25J 9/1676 | 700/255 |
| 2015/0223890 A1* | 8/2015 | Miller | A61B 50/10 | 726/17 |

(Continued)

FOREIGN PATENT DOCUMENTS

| | | | |
|---|---|---|---|
| DE | 102014219077 | A1 | 3/2016 |
| EP | 2380496 | A1 | 10/2011 |

(Continued)

OTHER PUBLICATIONS

International Preliminary Report on Patentability for Application No. PCT/US2020/035237 mailed on Dec. 9, 2021, 14 pages.

(Continued)

*Primary Examiner* — Abby Lin
*Assistant Examiner* — Renee LaRose

(57) ABSTRACT

A bifurcated navigation control system is configured to identify a navigation condition associated with a navigation of a component of a computer-assisted medical system component along a path from an initial location to a target location; determine, based on the navigation condition, a propulsion limitation configured to be imposed on operator-provided commands related to a propulsion of the component during the navigation of the component along the path; and direct the component to navigate, in a bifurcated navigation control mode, along at least part of the path from the initial location to the target location. In the bifurcated (Continued)

navigation control mode, the bifurcated navigation control system is configured to autonomously control a steering of the component while allowing operator control of the propulsion of the component based on the operator-provided commands as limited by the propulsion limitation.

20 Claims, 13 Drawing Sheets

Related U.S. Application Data

(60) Provisional application No. 62/855,569, filed on May 31, 2019.

(56) References Cited

U.S. PATENT DOCUMENTS

| | | | | |
|---|---|---|---|---|
| 2016/0096270 | A1 | 4/2016 | Ibarz et al. | |
| 2016/0311116 | A1 | 10/2016 | Hill et al. | |
| 2018/0099412 | A1 | 4/2018 | Pinter et al. | |
| 2018/0110494 | A1 | 4/2018 | Hsieh | |
| 2020/0100846 | A1 * | 4/2020 | Huang | A61B 6/4458 |
| 2021/0153958 | A1 | 5/2021 | Meglan et al. | |
| 2022/0218432 | A1 | 7/2022 | Hannaford et al. | |

FOREIGN PATENT DOCUMENTS

| | | | |
|---|---|---|---|
| WO | WO-2014036549 | A2 | 3/2014 |
| WO | WO-2019204013 | A1 | 10/2019 |

OTHER PUBLICATIONS

International Search Report and Written Opinion for Application No. PCT/US2020/035237, mailed Sep. 23, 2020, 17 pages.

Vertut, J., and Coiffet, P., “Robot Technology: Teleoperation and Robotics Evolution and Development,” English translation, Prentice-Hall, Inc., Inglewood Cliffs, NJ, USA 1986, vol. 3A, 332 pages.

* cited by examiner

SYSTEMS AND METHODS FOR BIFURCATED NAVIGATION CONTROL OF A MANIPULATOR CART INCLUDED WITHIN A COMPUTER-ASSISTED MEDICAL SYSTEM

RELATED APPLICATIONS

The present application is a continuation of U.S. patent application Ser. No. 17/610,376, filed Nov. 10, 2021, which is a U.S. National Stage Application under 35 U.S.C. § 371 of International Application No. PCT/US2020/035237, filed May 29, 2020, which claims priority to U.S. Provisional Patent Application No. 62/855,569, filed May 31, 2019, each of which is hereby incorporated by reference in its entirety.

BACKGROUND INFORMATION

Medical operations, such as various types of surgical and non-surgical procedures, may be performed using computer-assisted medical systems. In some examples, such computer-assisted medical systems may include one or more carts. Example carts include auxiliary carts containing data processing systems, visualization systems, power generators, and so forth. Example carts also include manipulator carts each having one or more arms (e.g., robotic arms) configured for manipulating instruments used to carry out the medical operation, input device carts containing input devices, and the like. For instance, a manipulator cart may be positioned in proximity to a body being operated upon (e.g., a body of a patient, cadaver, training fixture, animal, or the like), and various types of medical operations may be performed on the body by way of the arms of the manipulator cart as directed by a medical practitioner (e.g., a clinician such as a surgeon, etc.) who is located at a control console that may be outside of the operational area. In this way, highly effective medical operations may be performed.

In preparation for such computer-assisted medical operations, a manipulator cart is typically navigated by a human operator from an initial location (e.g., a location where the manipulator cart has been kept when not in use and/or where the manipulator cart is draped and otherwise prepared for the operation) to a target location proximate to an operating table upon which the body is located that is to be operated upon. Unfortunately, however, various challenges (e.g., poor visibility afforded to the operator, obstacles on the path, narrow parameters characterizing the target location, target configuration, and/or target orientation of the manipulator cart, etc.) may make it difficult for the operator to effectively navigate the manipulator cart in an efficient manner.

SUMMARY

Systems and methods for bifurcated navigation control of a manipulator cart included within a computer-assisted medical system are described herein. For instance, one embodiment of such a bifurcated navigation control system is implemented as a computer-assisted medical system comprising a manipulator cart, a memory storing instructions, and a processor communicatively coupled to the memory and the manipulator cart and configured to execute the instructions. For example, the instructions may direct the processor to define a path whereby the manipulator cart is to navigate from an initial location to a target location and to identify a navigation condition associated with a navigation of the manipulator cart along the path from the initial location to the target location. Based on the navigation condition, the processor may define a propulsion limitation for the manipulator cart during the navigation of the manipulator cart along the path, and may direct the manipulator cart to navigate, in a bifurcated navigation control mode, along at least part of the path from the initial location to the target location. In some examples, in the bifurcated navigation control mode, the processor may be configured to execute the instructions to autonomously control a steering of the manipulator cart while allowing operator control of a propulsion of the manipulator cart in accordance with the propulsion limitation.

An exemplary embodiment of a bifurcated navigation control method may be performed by a bifurcated navigation control system. For example, the method includes defining a path whereby a manipulator cart included within a computer-assisted medical system is to navigate from an initial location to a target location. The method further includes identifying a navigation condition associated with a navigation of the manipulator cart along the path from the initial location to the target location. Based on the navigation condition, the method defines a propulsion limitation for the manipulator cart during the navigation of the manipulator cart along the path. The method also includes directing the manipulator cart to navigate, in a bifurcated navigation control mode, along at least part of the path from the initial location to the target location. In some examples, in the bifurcated navigation control mode, the bifurcated navigation control system may autonomously control a steering of the manipulator cart while allowing operator control of a propulsion of the manipulator cart in accordance with the propulsion limitation.

Yet another exemplary embodiment is implemented by a non-transitory, computer-readable medium storing instructions that, when executed, direct a processor of a computing device to perform operations described herein. For instance, the instructions may direct the processor to define a path whereby a manipulator cart included within a computer-assisted medical system is to navigate from an initial location to a target location, and to identify a navigation condition associated with a navigation of the manipulator cart along the path from the initial location to the target location. Based on the navigation condition, the instructions may further direct the processor to define a propulsion limitation for the manipulator cart during the navigation of the manipulator cart along the path, and to direct the manipulator cart to navigate, in a bifurcated navigation control mode, along at least part of the path from the initial location to the target location. In some examples, in the bifurcated navigation control mode, the instructions may direct the processor to autonomously control a steering of the manipulator cart while allowing operator control of a propulsion of the manipulator cart in accordance with the propulsion limitation.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
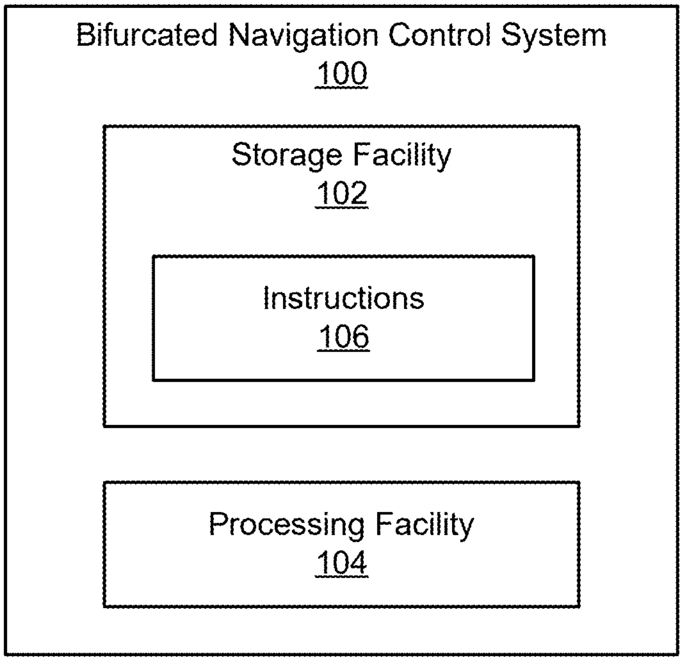
FIG. 1 illustrates an exemplary bifurcated navigation control system for bifurcated navigation control of a manipulator cart included within a computer-assisted medical system according to principles described herein.

Systems and methods for bifurcated navigation control of a manipulator cart included within a computer-assisted medical system are described herein. For example, in order to facilitate use of a manipulator cart to perform an operation, systems and methods described herein provide bifurcated navigation control modes that automatically assist an operator in navigating a manipulator cart from an initial location (e.g., a storage location) to a target location (e.g., a location at which the manipulator cart is ready for use in performing the operation). Systems and methods described herein also provide bifurcated navigation control modes that automatically assist an operator in navigating a manipulator cart from an initial orientation and/or configuration (e.g. a stowed configuration) to a target orientation and/or configuration (e.g. an orientation and/or a configuration at which the manipulator cart is ready for use in performing the operation). Examples of an operation that may be performed using an implementation of the manipulator carts described herein include medical procedures such as minimally invasive surgical or non-surgical procedures performed by way of an artificial or natural orifice in a body of a live human patient or another suitable body that may be living or non-living, biological or non-biological, natural or artificial, or the like (e.g., including but not limited to a body of an animal, of a cadaver, of a training fixture, etc.).

In a bifurcated navigation control mode, a processor autonomously controls a steering of the manipulator cart while allowing operator control of a propulsion of the manipulator cart using a control interface. For example, the operator may direct the manipulator cart forward or backward (e.g., at a speed acceptable to the operator) while the manipulator cart is autonomously steered along an appropriate path. In some examples, the propulsion of the manipulator cart in the bifurcated navigation control mode may be performed by operator control in accordance with a propulsion limitation applied by the system based on one or more navigation conditions associated with the navigation of the manipulator cart along the path.

In one implementation, for instance, a bifurcated navigation control system may be implemented by a computer-assisted medical system that includes a manipulator cart, a memory storing instructions, a processor communicatively coupled to the memory and configured to execute the instructions, and any other system components as may serve a particular implementation (examples of which will be described herein). The processor may be configured to execute the instructions to 1) define a path whereby the manipulator cart is to navigate from an initial location to a target location, 2) identify a navigation condition associated with a navigation of the manipulator cart along the path from the initial location to the target location, 3) define (e.g., based on the navigation condition) a propulsion limitation for the manipulator cart during the navigation of the manipulator cart along part of, or the entirety of, the path, and 4) direct the manipulator cart to navigate, in a bifurcated navigation control mode, along at least part of the path from the initial location to the target location. Once the manipulator cart arrives at a target location (and/or a target orientation or a target configuration, as applicable), an operation may be performed. An example target orientation and configuration for the manipulator cart is with the manipulator cart facing a target object with the manipulator arms positioned in a desirable way. An example target configuration for a kinematic structure of the manipulator cart is with one or more joints or links of the kinematic structure at target positions or orientations, or within a range of target positions or orientations, etc., for those joints or links.

As mentioned above, in the bifurcated navigation control mode, the processor may be configured to execute the instructions to autonomously control a steering of the manipulator cart while allowing operator control of a propulsion of the manipulator cart. This operator control of the propulsion may be allowed, in some examples, only in accordance with a propulsion limitation during some periods of propulsion, or during the entirety of propulsion. In other words, an operator may be in control of the propulsion while the system imposes a limitation on the propulsion that is based on one or more navigation conditions, given the applicable navigation conditions under those circumstances.

As used herein, a "propulsion limitation" may refer to any one or combination of limitations that a navigation control system may impose on the operator-commanded propulsion, which is the operator provided commands related to the propulsion of a manipulator cart other than steering commands. For example, a propulsion limitation may affect the magnitude of velocity (e.g. speed), the magnitude of acceleration, the magnitude of further derivatives of velocity or acceleration, etc. As described herein, a propulsion limitation can be set based on one or more navigation conditions. For example, a propulsion limitation may include an upper (i.e., maximum) speed limit imposed on the manipulator cart (i.e., such that the system does not allow the manipulator cart propulsion to be at a speed higher than the limit, which in some cases may mean that the manipulator cart propulsion is not as high as commanded by an operator-commanded propulsion), a lower (i.e., minimum) speed limit, an upper acceleration limit imposed on the manipulator cart (i.e., such that the system does not allow the manipulator cart propulsion to accelerate at an acceleration rate higher than the limit, which in some cases may mean that the manipulator cart propulsion is not as high as commanded by the operator-commanded propulsion), a lower acceleration limit, or another such limit as may be appropriate given one or more navigation conditions.

In some examples, the propulsion limitation may be quantized, such that operator-commanded propulsion meeting one or more first criteria (e.g. in a first propulsion magnitude range) are subject to a first type of propulsion limit (e.g. a first speed limit) and operator-commanded propulsion meeting one or more second criteria (e.g. in a second propulsion magnitude range) are subject to a second propulsion limitation type (e.g. a second speed limit). As a specific example, quantized propulsion limitation may thus quantize a speed commanded by the operator to one of a plurality of speed levels (e.g., a low speed, a medium speed, a high speed, etc.) at which the manipulator cart will actually be propelled as it is navigated. In the same or other examples, a propulsion limitation may be implemented in accordance with a transfer function that relates the operator-commanded propulsion to the manipulator cart propulsion. For example, transfer functions may relate system-implemented manipulator cart speed to operator-commanded speed or velocity, system-implemented magnitude of manipulator cart acceleration to operator-commanded acceleration, etc.). For instance, if navigation conditions dictate that speed or acceleration of a manipulator cart should be lower than commanded by the operator (e.g., while navigating a particular part of a path, while in a particular area or near particular obstacles, etc.), a bifurcated navigation control system may impose a propulsion limitation in accordance with a linear transfer function by directing the speed or acceleration of the manipulator cart to be a particular percentage (e.g., 50%, 75%, etc.) of the speed or acceleration commanded by the operator. The transfer functions can be partially or entirely linear, or partially or entirely non-linear.

It will be understood that limitations on the propulsion of a manipulator cart due to hardware limits (e.g., a maximum torque or speed rating of a motor used for driving the manipulator cart, etc.), or due to design of the manipulator cart (e.g., mass of the cart, size of the wheels, friction in the drive train, etc.) are not referred to herein as propulsion limitations based on navigation conditions because these limitations are not defined during operation based on navigation conditions. Similarly, global control-system-imposed limits on propulsion that are not defined during operation based on navigation conditions (e.g., a maximum speed of the cart to avoid burning out motors, a maximum turning rate to reduce the likelihood of injuries in collisions with people, etc.) are also not referred to herein as propulsion limitations based on navigation conditions. Similarly, features of certain manipulator carts that cause the manipulator cart to indicate a system fault and stop all motion, or to completely shut down, will also be understood to be outside the scope of propulsion limitations based on navigation conditions. Various examples of navigation conditions and corresponding propulsion limitations based on navigation conditions will be described in more detail below. As one example, a propulsion limitation defined based on a navigation condition of a shape of a turn in the path may include a maximum speed limit for the manipulator cart that will reduce or eliminate the likelihood that the manipulator cart will tip while traversing the turn.

Aspects of the bifurcated navigation control systems and methods described herein are primarily described with respect to manipulator carts such as might be included within a computer-assisted medical system. It will be understood, however, that principles described herein in relation to manipulator carts (or similar principles) may likewise apply to other types of carts and/or navigable system components. For instance, bifurcated navigation control of carts and system components such as auxiliary systems of a computer-assisted medical system (e.g., auxiliary carts, visualization systems, power generators, etc.), other navigable components of a computer-assisted medical system (e.g., a user control system, etc.), or other suitable navigable components associated with other types of systems (e.g., systems used for non-medical purposes and not described herein, etc.) may be performed using the principles described herein or similar principles.

Moreover, while aspects of the bifurcated navigation control systems and methods described herein primarily relate to implementations employing a computer-assisted medical system (e.g., a minimally invasive surgical system), it will be understood that inventive aspects disclosed herein may be embodied and implemented in various ways, including by employing robotic and non-robotic embodiments and implementations. Implementations relating to surgical or other medical systems are merely exemplary and are not to be considered as limiting the scope of the inventive aspects disclosed herein. For example, any reference to surgical instruments, surgical techniques, and/or other such details relating to a surgical context will be understood to be non-limiting as the instruments, systems, and methods described herein may be used for medical treatment or diagnosis, cosmetic improvements, imaging of human or animal anatomy, gathering data from human or animal anatomy, setting up or taking down systems, training medical or non-medical personnel, and so forth (any of which may or may not also involve surgical aspects). In other examples, the instruments, systems, and methods described herein may also be used for procedures performed on, or with, animals, human cadavers, animal cadavers, portions of human or animal anatomy, tissue removed from human or animal anatomies (which may or may not be re-implanted within the human or animal anatomy), non-tissue work pieces, training models, and so forth. In yet other examples, the instruments, systems, and methods described herein may be applied for non-medical purposes including for industrial systems, general robotics, teleoperational systems, and/or sensing or manipulating non-tissue work pieces.

Various benefits may be provided by the bifurcated navigation control systems and methods described herein. For example, navigation of a manipulator cart by way of a computer-assisted bifurcated navigation control mode such as those described herein may result in more effective and accurate positioning of the manipulator cart, in a safer manner with less risk of equipment damage, and in a more timely manner than when standard navigation control modes (i.e., navigation control modes in which an operator entirely directs both steering and propulsion of the manipulator cart) are employed. Different types of operations may require different cart placements in relation to the body to be operated upon, and, in certain examples, operators tasked with navigating the manipulator cart may not be intimately involved in certain aspects of the operation such that these operators may not fully understand the ideal target placement (e.g., target location, target orientation, target configuration, etc.) of the manipulator cart. Additionally, because every minute in a typical surgical operating room is costly, it is important that as little time as possible be lost in navigating a manipulator cart to its target location (and/or target orientation or target configuration, as applicable). As a result, conventional navigation of manipulator carts to the target location may suffer from either or both of suboptimal placement (e.g., a non-ideal or inaccurate final placement of the manipulator cart for a given operation type) and inefficient placement (e.g., an ideal or non-ideal placement that takes more time than is necessary to achieve). It is a significant benefit, therefore, that systems and methods described herein facilitate manipulator cart navigation in a manner that results in both optimal and efficient manipulator cart placement.

Another exemplary benefit of the systems and methods described herein is that a human operator retains propulsion control of the manipulator cart navigation even as the system autonomously handles the steering control and imposes appropriate propulsion limitations. It may be impractical or otherwise undesirable for the navigation of a manipulator cart to be fully automated such that both steering and propulsion are autonomously controlled. For example, it may be desirable (e.g., for efficiency reasons, safety reasons, etc.) for one or more human operators to always be directly involved in the movement of a large, heavy, valuable piece of equipment such as a manipulator cart. Accordingly, by bifurcating the steering and propulsion control of the manipulator cart, such that the steering is performed autonomously by the system while the propulsion control of the manipulator cart is performed by a human operator with system-imposed propulsion limitations, an effective and efficient navigation and positioning of the manipulator cart may be consistently achieved in a convenient, safe, and cost-effective way that is partially or entirely independent of the operator's specific knowledge of the ideal cart placement for a given operation type.

Certain specific benefits also arise from the propulsion limitations applied by systems and methods described herein to allow for operator control of the propulsion of the manipulator cart in accordance with certain propulsion limitations. For example, an operator may consistently direct propulsion to occur at whatever speed seems most appropriate to the operator, without concern about whether the commanded speed might result in problematic manipulator cart propulsion. This may allow the operator to accelerate the manipulator cart without worrying about commanding the manipulator cart to engage in propulsion (e.g., to move at a speed, to accelerate at a rate, etc.) that could burn out a motor of the manipulator cart. This may also allow the operator to navigate around obstacles without worrying about commanding the manipulator cart to engage in propulsion that would risk tipping the manipulator cart (e.g., if the manipulator cart is turning at too high a speed). In some implementations, this may also allow the operator to direct propulsion at a relatively high speed without worrying that a movable component of the manipulator cart (e.g., a boom, a manipulator arm, etc.) will not be adjusted (e.g., raised, lowered, etc.) in time to avoid hitting an obstacle, and so forth. The propulsion limitations may be used to disallow commanded acceleration, speed, or any other propulsion parameter that is unsafe or otherwise unadvisable.

Various embodiments will now be described in more detail with reference to the figures. The systems and methods described herein may provide one or more of the benefits mentioned above as well as various additional and/or alternative benefits that will be made apparent by the description below.

FIG. 1 illustrates an exemplary bifurcated navigation control system 100 ("system 100") for bifurcated navigation control of a manipulator cart included within a computer-assisted medical system. As will be described and illustrated in more detail below, a "manipulator cart," as used herein, may refer to any robotic or other system that includes one or more manipulators (e.g., manipulator arms, etc.) configured to facilitate performance of an operation (e.g., a medical operation such as a surgical procedure, etc.), and that is configured to be independently navigable from one location to another, rather than being mounted, for example, on a physical track.

As shown, system 100 may include, without limitation, a storage facility 102 and a processing facility 104 selectively and communicatively coupled to one another. Facilities 102 and 104 may each include or be implemented by hardware and/or software components (e.g., processors, memories, communication interfaces, instructions stored in memory for execution by the processors, etc.).

In some examples, facilities 102 and 104 may be integrated into a single device (e.g., a manipulator cart control system, etc.), while, in other examples, facilities 102 and 104 may be distributed between multiple devices and/or multiple locations as may serve a particular implementation. For instance, in one implementation of system 100, the manipulator cart itself may include one or more built-in processors, data storage devices, sensors, communication interfaces, and so forth for implementing system 100. In contrast, in other implementations of system 100, some or all of these components may not be integrated into the manipulator cart itself but, rather, may be implemented on other computing systems as may serve a particular implementation (e.g., edge servers, cloud servers, computing devices integrated with other components of a computer-assisted medical system that includes the manipulator cart, etc.).

Storage facility 102 may maintain (e.g., store) executable data used by processing facility 104 to perform any of the functionality described herein. For example, storage facility 102 may store instructions 106 that may be executed by processing facility 104 to perform any of the functionality described herein. Instructions 106 may be implemented by any suitable application, software, code, and/or other executable data instance. Storage facility 102 may also maintain any data received, generated, managed, used, and/or transmitted by processing facility 104.

Processing facility 104 may be configured to perform (e.g., execute instructions 106 stored in storage facility 102 to perform) various processing functions associated with bifurcated navigation control of the manipulator cart. For example, processing facility 104 may define a path whereby the manipulator cart is to navigate from an initial location to a target location. Processing facility 104 may also direct the manipulator cart to identify a navigation condition associated with a navigation of the manipulator cart along the path from the initial location to the target location, and to define, based on the navigation condition, a propulsion limitation for the manipulator cart during the navigation of the manipulator cart along the path. Processing facility 104 may direct the manipulator cart to navigate along at least part of the path from the initial location to the target location in a bifurcated navigation control mode that accounts for the propulsion limitation that was defined. For example, in the bifurcated navigation control mode, processing facility 104 may be configured to autonomously control a steering of the manipulator cart while allowing operator control of a propulsion of the manipulator cart in accordance with the propulsion limitation.

To this end, processing facility 104 may autonomously control a steering of the manipulator cart while allowing operator control of a propulsion of the manipulator cart (within limits set by the propulsion limitation) using a control interface. As used herein, controlling the "steering" of a manipulator cart may refer to some or all aspects of navigation control that involve defining the direction in which motion vectors are directed (e.g., which way the wheels of the manipulator cart are pointing, etc.). For example, using a standard automobile as an analogy, the steering control of an automobile may relate to the control of the automobile imposed by way of the steering wheel. In contrast, controlling the "propulsion" of a manipulator cart may refer to some or all aspects of navigation control that involve defining the magnitude and/or sign (e.g., positive or negative) of the motion vectors (e.g., whether and to what degree the wheels of the manipulator cart are turning in either a forward or backward direction). For example, referring again to the automobile analogy, the propulsion control of the automobile may be performed by way of the gas pedal, the brake, and/or the gear shift (e.g., whether the automobile is in a "park" mode, a "drive" mode, a "reverse" mode, etc.).

Processing facility 104 may perform the functions described above and other functions described herein in any suitable manner, as will be described in more detail below. Additionally, in an analogous way as described above in relation to the location of the manipulator cart, processing facility 104 may, in certain embodiments involving target orientations and/or target configurations, direct the manipulator cart, in a first bifurcated navigation control mode, from an initial orientation and/or initial configuration to a target orientation and/or target configuration along with guiding the manipulator cart from the initial location to the target location.

In some implementations, system 100 (e.g., processing facility 104) may be configured to provide bifurcated navigation control of a manipulator cart in real time. As used herein, a function may be said to be performed in real time when the function relates to or is based on dynamic, time-sensitive information and the function is performed while the time-sensitive information remains accurate or otherwise relevant. Due to processing times, communication latency, and other inherent delays in physical systems, certain functions may be considered to be performed in real time when performed immediately and without undue delay, even if performed after small delay (e.g., a delay up to a few seconds or the like). As one example of real-time functionality, processing facility 104 may define a path based on the real-time states of obstacles in between the initial location and the target location, and may update the path as the state of obstacles changes. As another example of real-time functionality, in some embodiments where target orientations and/or configurations exist for the manipulator cart, processing facility 104 may define changes in cart orientation and/or configuration to achieve target orientations and/or configurations based on real-time states of obstacles.

System 100 may be used in various contexts with various different types of technologies as may serve a particular implementation. For example, system 100 may be used in a medical context such as in preparation for a computer-assisted medical procedure in which an operation is performed inside of any suitable type of body described herein. In other implementations, system 100 may be used in medical contexts that are not surgical in nature (e.g., diagnostic or exploratory imaging without surgical elements), or that are not for treatment or diagnosis (e.g., training or other procedures where such procedures do not involve treatment). Additionally, in certain implementations, system 100 may be used in non-medical contexts. For instance, system 100 may be useful for navigating other types of large, free-moving objects that may or may not fall under the category of a manipulator cart, as that term is used herein.

To illustrate an exemplary context in which system 100 may be implemented and employed, an exemplary computer-assisted medical system that implements system 100 and includes a manipulator cart will now be described. The computer-assisted medical system described below is illustrative and not limiting. It will be understood that bifurcated navigation control systems and methods described herein may operate as part of or in conjunction with the computer-assisted medical system described herein, with other suitable computer-assisted medical systems that may or may not be surgical systems, and/or with other suitable medical and/or non-medical systems as may serve a particular implementation.

Figure 2:
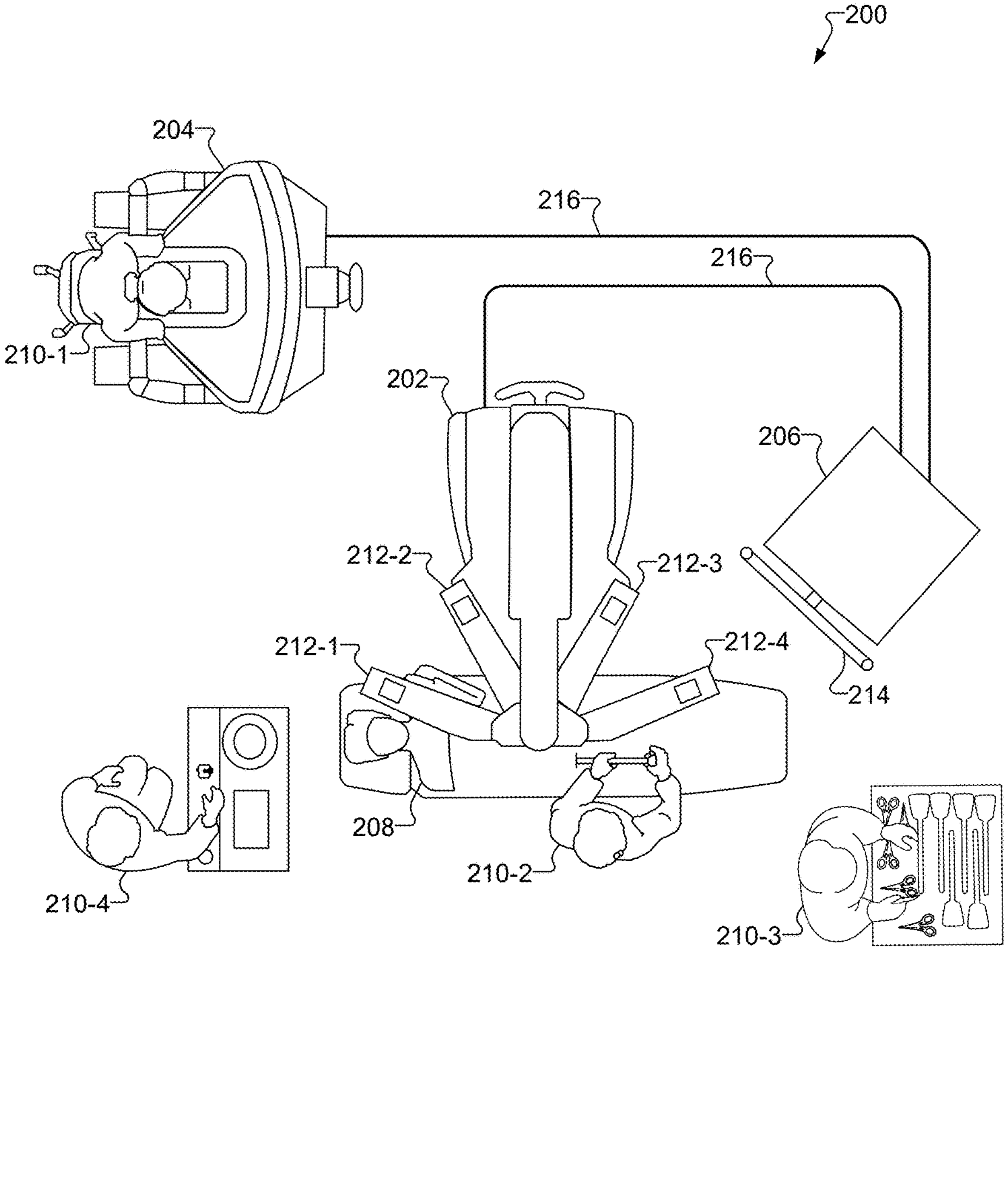
FIG. 2 illustrates an exemplary computer-assisted medical system according to principles described herein.

FIG. 2 illustrates an exemplary computer-assisted medical system 200 ("medical system 200") that may be used to perform surgical and/or non-surgical medical procedures. As shown, medical system 200 may include a manipulator cart 202, a user control system 204, and an auxiliary system 206 communicatively coupled one to another. Medical system 200 may be utilized by a medical team to perform a computer-assisted medical procedure or other such operation on a body of a patient 208 or on any other body as may serve a particular implementation. As shown, the medical team may include a first clinician 210-1 (such as a surgeon for a surgical procedure), an assistant 210-2, a nurse 210-3, and a second clinician 210-4 (such as an anesthesiologist for a surgical procedure), all of whom may be collectively referred to as "team members 210," and each of whom may control, interact with, or otherwise be a user of medical system 200. Additional, fewer, or alternative team members may be present during a medical procedure as may serve a particular implementation. For example, for some medical procedures, the "clinician 210-1" may not be a medical doctor. Further, team composition for non-medical procedures would generally be different and would include other combinations of members serving non-medical roles.

While FIG. 2 illustrates an ongoing minimally invasive medical procedure such as a minimally invasive surgical procedure, it will be understood that medical system 200 may also be used to perform open medical procedures or other types of operations that may benefit from the accuracy and convenience of medical system 200. For example, operations such as exploratory imaging operations, mock medical procedures used for training purposes, and/or other operations may also be performed using medical system 200.

As shown in FIG. 2, manipulator cart 202 may include a plurality of manipulator arms 212 (e.g., arms 212-1 through 212-4) to which a plurality of instruments (e.g., surgical instruments, other medical instruments, or other instruments) may be coupled. Each instrument may be implemented by any suitable surgical tool (e.g., a tool having tissue-interaction functions), medical tool, imaging device (e.g., an endoscope), sensing instrument (e.g., a force-sensing instrument), diagnostic instrument, or the like that may be used for a computer-assisted medical procedure such as a surgical procedure on patient 208 (e.g., by being at least partially inserted into patient 208 and manipulated to perform a computer-assisted medical procedure on patient 208). While manipulator cart 202 is depicted and described herein as including four manipulator arms 212, it will be recognized that manipulator cart 202 may include only a single manipulator arm 212 or any other number of manipulator arms as may serve a particular implementation. Additionally, it will be understood that, in some exemplary systems, certain instruments may not be coupled to or controlled by manipulator arms, but rather may be handheld and controlled manually (e.g., by a surgeon, other clinician, or other medical personnel). For instance, certain handheld devices of this type may be used in conjunction with or as an alternative to computer-assisted instrumentation that is coupled to manipulator arms 212 shown in FIG. 2.

Manipulator arms 212 and/or instruments attached to manipulator arms 212 may include one or more displacement transducers, orientational sensors, and/or positional sensors used to generate raw (i.e., uncorrected) kinematics information. One or more components of medical system 200 may be configured to use the kinematics information to track (e.g., determine positions of) and/or control the instruments.

During the medical operation, user control system 204 may be configured to facilitate control by clinician 210-1 of manipulator arms 212 and instruments attached to manipulator arms 212. For a surgical procedure, for example, clinician 210-1 may be a surgeon. Clinician 210-1 may interact with user control system 204 to remotely move or manipulate manipulator arms 212 and the instruments. To this end, user control system 204 may provide clinician 210-1 with imagery (e.g., high-definition 3D imagery) of an operational area associated with patient 208 as captured by an imaging device. In certain examples, user control system 204 may include a stereo viewer having two displays where stereoscopic images of an internal view of the body of patient 208 generated by a stereoscopic imaging device may be viewed by clinician 210-1. Clinician 210-1 may utilize the imagery to perform one or more procedures with one or more instruments attached to manipulator arms 212.

To facilitate control of instruments, user control system 204 may include a set of master controls. These master controls may be manipulated by clinician 210-1 to control movement of instruments (e.g., by utilizing robotic and/or teleoperation technology). The master controls may be configured to detect a wide variety of hand, wrist, and finger movements by clinician 210-1. In this manner, clinician 210-1 may intuitively perform a procedure using one or more instruments.

Auxiliary system 206 may include one or more computing devices configured to perform processing operations of medical system 200. In such configurations, the one or more computing devices included in auxiliary system 206 may control and/or coordinate operations performed by various other components of medical system 200 such as manipulator cart 202 and/or user control system 204. For example, a computing device included in user control system 204 may transmit instructions to manipulator cart 202 by way of the one or more computing devices included in auxiliary system 206. As another example, auxiliary system 206 may receive and process image data representative of imagery captured by an imaging device attached to one of manipulator arms 212.

In some examples, auxiliary system 206 may be configured to present visual content to team members 210 who may not have other access to the images provided to clinician 210-1 at user control system 204. To this end, auxiliary system 206 may include a display monitor 214 configured to display one or more user interfaces, one or more images (e.g., 2D images) of the operational area, information associated with patient 208 and/or the medical procedure, and/or any other content as may serve a particular implementation. In some examples, display monitor 214 may display images of an internal view of the operational area together with additional content (e.g., graphical content, contextual information, etc.). Display monitor 214 may be implemented by a touchscreen display with which team members 210 may interact (e.g., by way of touch gestures) to provide user input to medical system 200, or may be implemented by any other type of display screen as may serve a particular implementation.

As will be described in more detail below, system 100 may be implemented within or may operate in conjunction with medical system 200. For instance, in certain implementations, system 100 may be implemented entirely by manipulator cart 202, or by sensors and/or computing components implemented by one or more other components of medical system 200.

Manipulator cart 202, user control system 204, and auxiliary system 206 may be communicatively coupled one to another in any suitable manner. For example, as shown in FIG. 2, manipulator cart 202, user control system 204, and auxiliary system 206 may be communicatively coupled by way of control lines 216, which may represent any wired or wireless communication link as may serve a particular implementation. To this end, manipulator cart 202, user control system 204, and auxiliary system 206 may each include one or more wired or wireless communication interfaces, such as one or more local area network interfaces, Wi-Fi network interfaces, cellular interfaces, and so forth.

Figure 3:
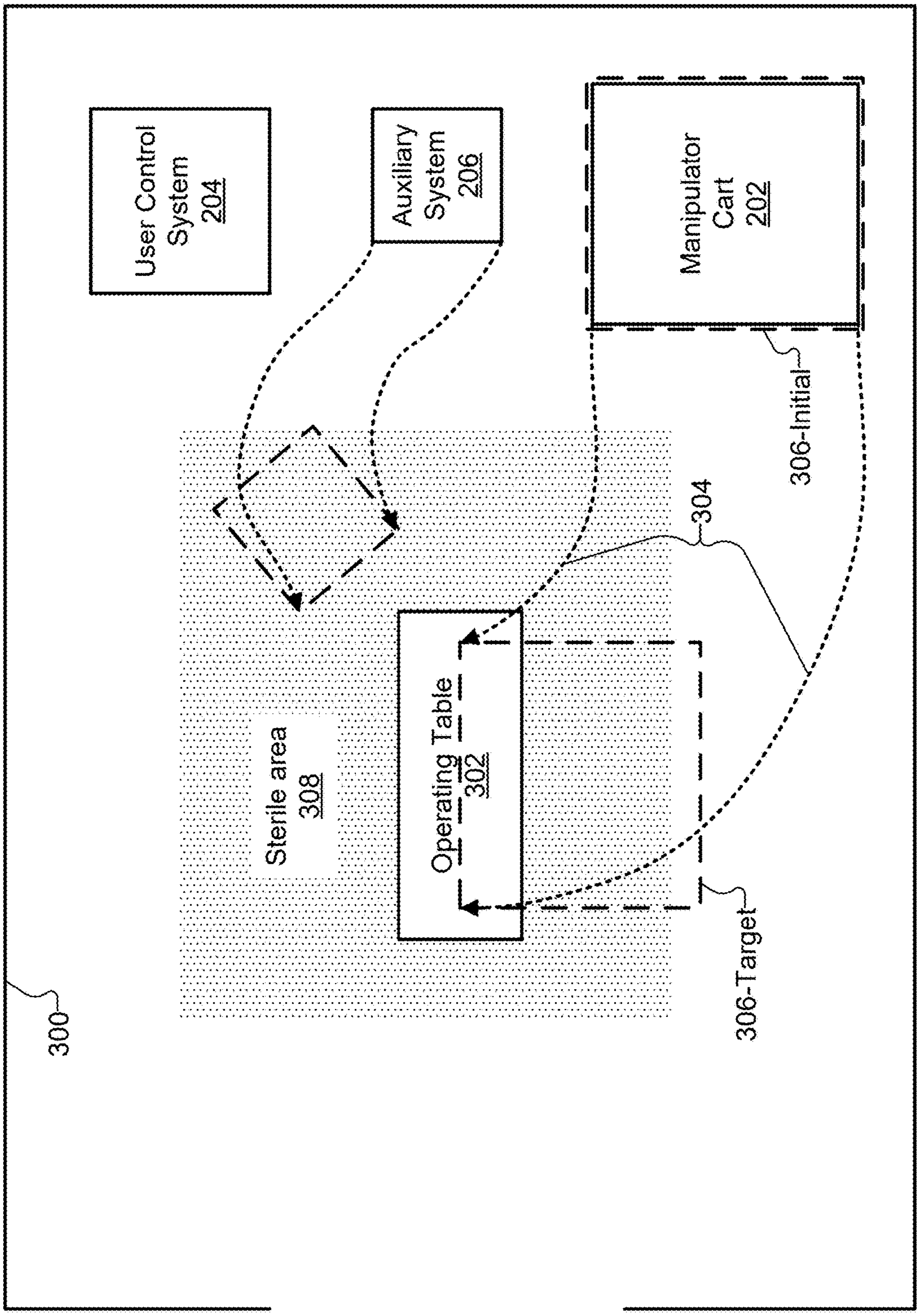
FIGS. 3 and 4 illustrate respective exemplary operating rooms within which an exemplary manipulator cart is to be navigated along an exemplary path from an initial location to a target location according to principles described herein.

To illustrate a specific environment and scenario in which system 100 may be employed to perform bifurcated navigation control of a manipulator cart such as manipulator cart 202, FIG. 3 shows an exemplary operating room 300 within which manipulator cart 202 is to be navigated toward an operating table 302 along an exemplary path 304 that extends from an initial location 306-initial to a target location 306-target. Operating room 300 provides an environment in which, under direction of one or more members of a medical operation team (e.g., team members 210), medical system 200 is configured to perform a medical operation on a body located on operating table 302.

FIG. 3 depicts a relatively small operating room 300 with a relatively simple layout. Specifically, as shown, location 306-initial is located relatively close to location 306-target within operating room 300, and there are not shown any obstacles between locations 306-initial and 306-target. As a result, path 304 is shown to be relatively straightforward as a path with a single gentle curve.

System 100 may define locations 306 (e.g., location 306-initial and 306-target), as well as other locations described herein, based on any suitable coordinate system or other formal or informal spatial characterization. For instance, a global coordinate system relative to operating table 302, a door or center of operating room 300, a storage location of manipulator cart 202, or any other suitable origin point may be defined, and locations 306 may be defined and analyzed with respect thereto.

As shown, location 306-initial may be a location that is tucked out of the way in a corner of operating room 300. For example, this location may be a storage location for manipulator cart 202 when medical system 200 is not in use (e.g., between medical operations, when a non-computer-assisted medical operation is being performed on operating table 302, etc.). Location 306-initial may also or alternatively be a preparation location for manipulator cart 202 where manipulator cart 202 may be covered with drapes and/or otherwise be sterilized and prepared to enter a sterile field 308 of operating room 300 in which the operation is to be performed.

Location 306-target may be a location that is relatively proximate to operating table 302. Specifically, location 306-target may be positioned where manipulator cart 202 is to be located during performance of the medical operation on the body, therefore making location 306-target nearer than location 306-initial to operating table 302. As depicted in FIG. 3, location 306-target may overlap with operating table 302 from the top view because arms 212 incorporated within manipulator cart 202 may hover over operating table 302 when manipulator cart 202 is in an operative position at operating table 302. In some examples, location 306-target may be specifically selected by an operator of manipulator cart 202 (e.g., by selecting a point on a map, by selecting one of a plurality of predetermined locations for manipulator cart 202 that are associated with different operations, etc.). In other examples, however, location 306-target may be automatically selected by system 100. For instance, location 306-target may be automatically selected in a manner that accounts for an operation type that is to be performed, photographic input representative of the room layout, a detected or expected location of cannulas on the body, gestures indicating the location by a person in a vicinity of the target area (e.g., gesturing by a bedside surgical team member), and/or any other criteria as may serve a particular implementation.

Other components of medical system 200 are also shown to be located in operating room 300 along with manipulator cart 202. For example, user control system 204 is shown to be statically located in another corner of operating room 300 in this example (although it will be understood that user control system 204 may, in certain examples, be mobile), and auxiliary system 206 is shown to similarly be moved from an initial location that is away from the target location (e.g. which can be a storage location, a preparation location at the side of operating room 300, a temporary parking location, etc.) to a target location within sterile field 308 near operating table 302. It will be understood that other people and objects not explicitly shown may also be present within operating room 300, although, for purposes of this example, it is understood that there is not any significant obstacle on or near path 304 between locations 306-initial and 306-target.

In the scenario illustrated in FIG. 3, both locations 306-initial and 306-target are relatively proximate to one another within operating room 300. As such, path 304 has a clear beginning and a clear end and is fully contained within operating room 300. In other examples, however, it will be understood that one or both of the initial and target locations may not be located within the same room as one another, or the initial and/or target locations associated with a path may not yet be explicitly designated while manipulator cart 202 is navigating along the path. For instance, in one example, manipulator cart 202 may be located external to operating room 300 (e.g., in a different operating room, in a storage closet outside operating room 300, etc.) such that the initial location of manipulator cart 202 is external to room 300 and the target location (in this case, a location within room 300 where manipulator cart 202 will be draped and sterilized) is not designated until manipulator cart 202 enters operating room 300. Analogously, it will be understood that an initial location and a target location may be swapped so that manipulator cart 202 may be rolled back out of the way of the medical operation location, to a storage location, to another operating room, etc. For instance, after the operation at operating table 302 is complete or if an emergency egress is initiated for manipulator cart 202, manipulator cart 202 may be configured to navigate back along path 304 in similar (but opposite) manner as described above for navigating forward along path 304.

Figure 4:
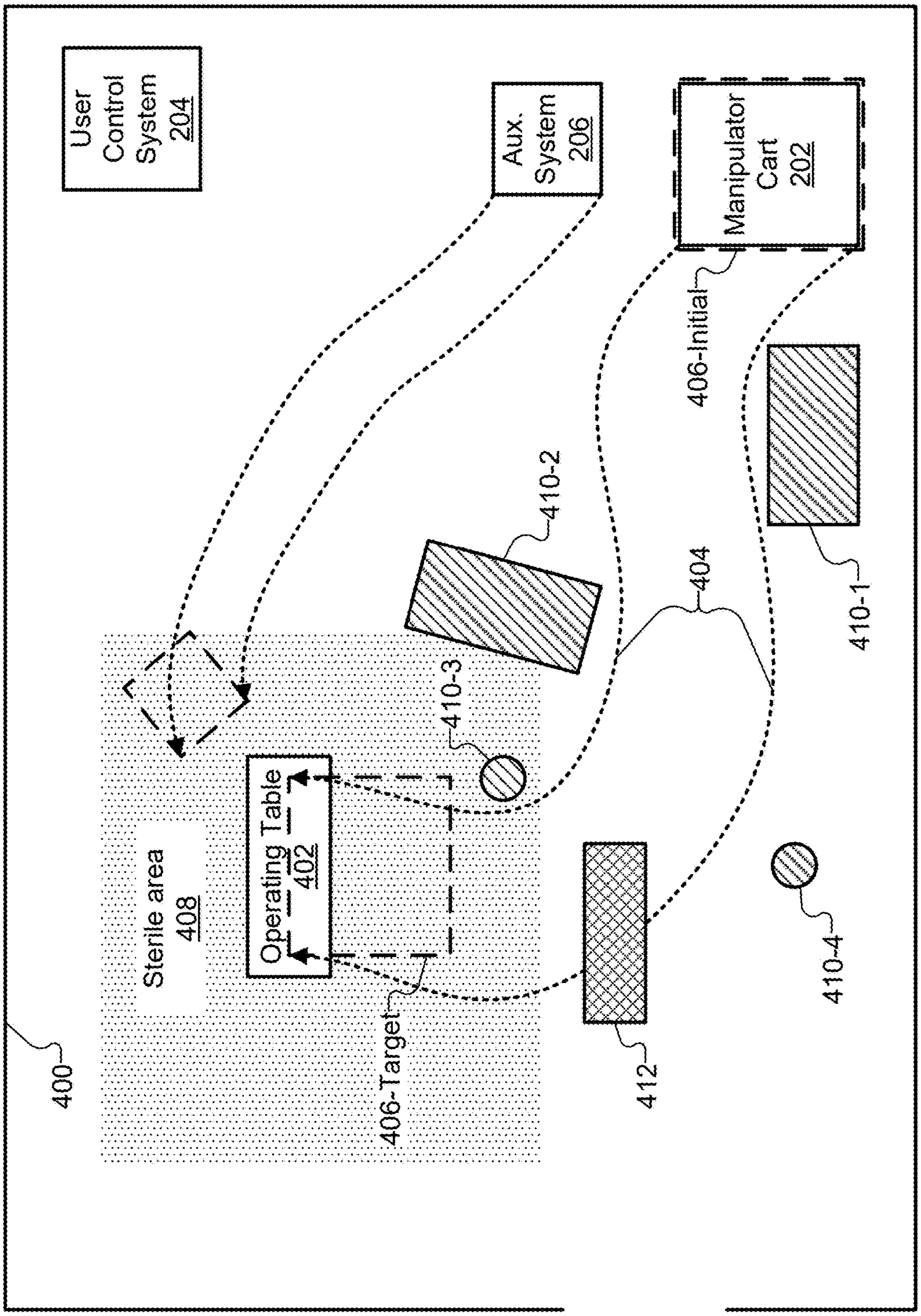

FIG. 4 shows another exemplary operating room 400 within which manipulator cart 202 is to be navigated toward an operating table 402 via an exemplary path 404 from an initial location 406-initial to a target location 406-target near operating table 402 within a sterile field 408. The scenario illustrated in FIG. 4 is similar to that shown in FIG. 3, and each the of the principles described in relation to FIG. 3 may similarly apply in the context of FIG. 4. However, operating room 400 of FIG. 4 is shown to be considerably more complex than operating room 300 of FIG. 3. For example, a plurality of obstacles 410 (e.g., obstacles 410-1 through 410-4) that must be avoided or otherwise accounted for in the planning of path 404 are located on the ground between locations 406-initial and 406-target. Moreover, an obstacle 412 that is shaded in with a different hatch-line pattern than obstacles 410 will be understood to represent an overhead obstacle that also must be accounted for in the defining of path 404.

As described above, system 100 may be configured to define path 404 from location 406-initial to location 406-target to thereby allow system 100 to autonomously control the steering of manipulator cart 202 as an operator controls the propulsion (in accordance with any propulsion limitations that may be imposed) in the bifurcated navigation control mode. This path may be defined in any manner as may serve a particular implementation. For example, system 100 may further comprise (e.g. as part of or in addition to facilities 102 and 104) at least one sensor such as a visual light image sensor (e.g., a camera, a video capture device, etc.), an infrared image sensor, a depth sensor (e.g., a time-of-flight ("TOF") sensor, a Light Detection and Ranging ("LIDAR") sensor, an ultrasonic sensor, a radar sensor, a laser range finder, etc.), or any other sensor configured to detect characteristics of the natural world in a manner that facilitates the defining of a path for manipulator cart 202. Such sensors may be integrated with manipulator cart 202 itself (e.g., such as by being mounted on arms 212 or a base or other part of manipulator cart 202), or may be integrated with other components of medical system 200 or otherwise located in operating room 400 independently from manipulator cart 202 (e.g., mounted on the wall, attached to operating table 402, etc.).

In examples where system 100 includes or is in communication with one or more of these types of sensors, system 100 may perform the defining of path 404 by receiving sensor data from the at least one sensor and defining the path based on the received sensor data. For example, system 100 may receive image data and/or depth data from one or more vantage points and representative of real-time locations of obstacles 410 and/or 412. Consequently, system 100 may define path 404 in a manner that attempts to avoid or otherwise appropriately handle each of obstacles 410 and/or 412 that the sensors detect.

As system 100 plans and defines path 404 whereby manipulator cart 202 is to navigate from location 406-initial to location 406-target, system 100 may account for various factors. For example, system 100 may detect an obstacle between location 406-initial and location 406-target (e.g., one of obstacles 410 or 412), determine a movability status of the obstacle, and account for the movability status of the obstacle in the defining of path 404. As used herein, a "movability status" associated with an obstacle may refer to characteristics of the obstacle related to how easily the obstacle may be relocated, how much free space is around the obstacle, whether the obstacle is limited in movement by cables connected to the obstacle, how likely the obstacle is to relocate on its own (e.g., whether the obstacle is a person who appears to have awareness of manipulator cart 202 and is likely to move out of the way), and so forth.

Accordingly, accounting for a movability status of an easily movable obstacle (e.g., a stool, an observer, etc.) may be done differently than accounting for a movability status of a more permanent or non-movable obstacle (e.g., an anesthesiologist station that is set up near the operating table, etc.). For instance, an easily movable obstacle may be accounted for by routing the path to go through the obstacle and then indicating to the operator that the obstacle should be moved out of the way, while a more permanent or less conveniently-movable obstacle may be accounted for by routing the path around the obstacle to avoid the obstacle altogether. In other examples, certain obstacles may be determined to be likely to move on their own (e.g., a person who crosses over the path but has a clear movement vector indicating that they will not remain on the path for long, etc.) and, at least while the obstacles are not immediately proximate to the manipulator cart, may be treated as a lower priority to avoid or may be ignored by system 100 altogether in the defining of path 404. Additionally, certain overhead obstacles (e.g., obstacle 412) may be accounted for by lowering an operating platform of manipulator cart 202 to a boom and arms 212 are attached. By lowering the operating platform in this way, overhead obstacles may be passed under rather than needing to be routed around.

As another exemplary factor for which system 100 may account when defining path 404, system 100 may, after detecting an obstacle between location 406-initial and location 406-target, determine a risk factor, and account for the risk factor in the defining of path 404. As used herein, a "risk factor" may refer to anything relating to an obstacle, a manipulator cart being navigated, the path being navigated, or any other aspect of the navigation that may be associated with adverse consequences. For example, one risk factor may be that if a speed of the propulsion is too high for a particular curve of the path, the manipulator cart could be at risk of tipping, causing damage to the manipulator cart. As another example, a risk factor associated with a particular obstacle may relate to consequences of the manipulator cart coming into contact with the particular obstacle as the manipulator cart traverses the path, thereby causing potential damage or a sterility breach to the manipulator cart and/or potential damage to the particular obstacle.

As such, accounting for a risk factor of an obstacle that is fragile or delicate, valuable or expensive to replace, or that is sterile and intended to remain so, may be done differently than accounting for a risk factor of an obstacle that is less consequential for manipulator cart 202 to come into contact with (e.g., a sterile object that a sterile manipulator arm may brush up against). For example, a delicate, expensive, or sterile obstacle may be accounted for by steering around the obstacle with a relatively wide margin to ensure that manipulator cart 202 does not contact the obstacle even if the obstacle moves or there is a miscalculation in navigating path 404. In contrast, an object that is not subject to any severe consequence if contacted by manipulator cart 202 (e.g., a stool that would just be bumped out of the way, etc.) may be accounted for by steering around the obstacle with a relatively narrow margin or no margin, thereby assuming the lower risk of negative consequence if minor contact is made.

In various examples, system 100 may account for obstacles by steering around the obstacles, requesting that the obstacles by manually moved (e.g., projecting a light of one color on an obstacle to be moved and a light of another color on obstacles that do not need to be moved), lowering the operating platform to pass under the obstacles, raising the operating platform so that arms attached to the boom pass over the obstacles, altering a pose of one or more arms (e.g., spreading or narrowing the spread of the arms, rotating the arms from one side of the cart to the other, lifting or lowering the arms, etc.), or in any other suitable way. Additionally, along with accounting for obstacles, system 100 may further account for other factors that affect the navigation of manipulator cart 202 along path 404. For example, system 100 may account for the width of manipulator cart 202 in determining a width of path 404 (e.g., including a margin), a turn radius of manipulator cart 202, which paths people moving about in operating room 400 tend to use to avoid obstacles, whether and how obstacles such as people are moving, how reconfigurable object surfaces are (e.g., distinguishing among solid, monolithic objects, objects with joints or flexible regions that allow bending and shape reconfiguration, objects covered by baggy drapes, etc.), and so forth.

In some implementations, system 100 may be configured to define and provide an operator with a plurality of path options, to thereby allow the operator to participate in the defining of path 404 by selecting one of the path options. Specifically, for example, the defining of path 404 by system 100 may include 1) defining a plurality of different paths whereby manipulator cart 202 could navigate from location 406-initial to location 406-target, and 2) selecting path 404 from the plurality of different paths and based on input from an operator. Additionally or alternatively, system 100 may request or accept additional operator input to define or revise path 404 in accordance with operator preferences.

In some scenarios (e.g., such as the relatively simple scenario illustrated in FIG. 3), it may be possible and desirable for system 100 to define an entire path (or a plurality of options for several entire paths) prior to manipulator cart 202 beginning to navigate along the path. In other examples, however, it may be difficult, impractical, impossible, or undesirable to define path 404 in its entirety at the outset in this way. This may be the case for a variety of reasons. For example, obstacles may be dynamically moving (e.g., some moving out of the way and others getting in the way after manipulator cart 202 has begun navigating). As another example, sensors may provide different characterizations (e.g., more comprehensive characterizations) from different locations along path 404 as different parts of the room become occluded or unoccluded from the vantage point of the sensors as the sensors move. Due to the dynamic and mobile nature of manipulator cart 202, as well as, in some examples, the dynamic and mobile nature of certain sensors and/or obstacles, system 100 may be configured to update path 404 while manipulator cart 202 is navigating along path 404, to dynamically provide different path options that may be identified or detected during navigation, or to otherwise dynamically alter path 404 as path 404 is being navigated.

System 100 may plan path 404 based on a predefined map of operating room 400 that system 100 accesses and that indicates the layout of operating room 400 (e.g., including wall placement, ceiling height and overhead obstacle height and layout, locations and configurations of permanent obstacles, the location and configuration of operating table 402, etc.). However, system 100 may also add to this predefined information a more dynamic analysis of temporary or new obstacles, dynamic docking considerations (e.g., detected locations of cannulas, etc.), and so forth. Sensors positioned in a manner that may be at least partially controlled by system 100 may be particularly useful for dynamic path definition. For example, sensors positioned on a boom or on individual arms 212 of manipulator cart 202 may be configured to continuously scan operating room 400 to capture new perspectives as manipulator cart 202 navigates along path 404. In some examples, system 100 may raise or lower an operating platform, rotate a boom to which arms 212 are attached, reposition a particular link or joint of an arm 212, or otherwise make adjustments to manipulator cart 202 in order to gather sensor data from different perspectives. In some examples, the predefined map of operating room 400 used by system 100 may have been generated (or may be generated in real time) by system 100 using simultaneous localization and mapping ("SLAM") techniques or other such techniques to build and update a three-dimensional model of operating room 400.

Even when system 100 has a degree of control over the sensors, it may not be possible in certain examples for system 100 to locate and positively identify location 406-target until manipulator cart 202 approaches the target location. As such, system 100 may direct, prior to the defining of path 404, manipulator cart 202 to be moved from a first location from which location 406-target is undetectable by a sensor of manipulator cart 202 to a second location from which location 406-target is detectable by the sensor. While manipulator cart 202 is at this second location, system 100 may determine that the sensor detects location 406-target and, in response to the determining that the sensor detects location 406-target, may designate the second location to be location 406-initial (i.e., the location at which path 404 begins).

FIG. 4 illustrates a path 404 that may be traversed by manipulator cart 202 by always using forward propulsion (i.e., moving in a forward direction). However, it will be understood that, in certain examples, an implementation of path 404 may be defined to include at least one portion in which manipulator cart 202 uses backward propulsion in order to progress along the path from the initial location to the target location. For example, the turning radius of the manipulator cart 202 may be larger than the radius of the turn needed by the path, and back-and-forth movement of the manipulator cart 202 while turning the manipulator cart 202 may allow the manipulator cart to achieve the sharper turn. As another example, an implementation of a path 404 may have a dead end from which manipulator cart 202 may need to be backed out (i.e., use backwards propulsion to move in a backwards direction) to traverse a new or revised path 404. In such examples, manipulator cart 202 may indicate to the operator that the operator should commanded propulsion in a reverse direction (e.g., begin pulling backwards rather than pushing forwards) in order to reach the target location. In further examples, a backwards portion of a path 404 may be planned into the path initially when the path is defined.

Medical system 200 is only shown to include a single manipulator cart 202 and, as shown by FIGS. 3 and 4, this manipulator cart 202 alone is presumed to perform manipulation tasks in connection with the operation being performed at operating tables 302 and 402. It will be understood, however, that in certain examples, more than one manipulator cart, or a manipulator cart and another equipment component of medical system 200, may both be navigated to the operating table for use in the operation. For example, medical system 200 may further include an additional equipment component besides manipulator cart 202 and the other equipment components illustrated in FIGS. 2-4, such as a second manipulator cart (e.g., a manipulator cart with more than, fewer than, or an equal number of, manipulator arms as manipulator cart 202), an equipment component that moves on a track or freely along a floor, an equipment component that moves through the air (e.g., a drone, etc.), or any other equipment component as may serve a particular implementation. In this example, the defining of the path may be performed to account for an additional path whereby the additional equipment component is to navigate from an additional initial location to an additional target location. For instance, path 404 may be defined so as to avoid not only obstacles 410 and 412, but also to not interfere with (or risk interference from) a path of one or more additional equipment components that may exist in a particular implementation of medical system 200 (not shown in FIG. 4). To this end, the defining of path 404 may account for the additional path based on locations of manipulator cart 202 and the additional equipment component, roles that manipulator cart 202 and the additional equipment component are to have in performing the operation at operating table 402, and so forth.

Along with directing a base of manipulator cart 202 to be navigated along path 404 from location 406-initial to location 406-target, system 100 may similarly be configured, in addition or as an alternative to the navigation of the base, to navigate and move other components of manipulator cart 202 in accordance with a predefined or dynamically defined path (e.g., path 404). That is, during navigation of manipulator cart 202 toward location 406-target and/or once the base of manipulator cart 202 has arrived at location 406-target, system 100 may further direct manipulator cart 202 to be reoriented to a target orientation. Alternatively or in addition, during navigation of manipulator cart 202 toward location 406-target and/or once the base of manipulator cart 202 has arrived at location 406-target, system 100 may further direct other movable components of manipulator cart 202 (e.g., an operating platform, a boom, one or more manipulator arms 212, etc.) to become reoriented, posed, and otherwise reconfigured as part of, in addition to, or as an alternative to the navigation of path 404. For instance, in certain examples, initial location 406-initial may be associated with an initial configuration of a movable component of manipulator cart 202, target location 406-target may be associated with a target configuration of the movable component of manipulator cart 202, and the defining of path 404 may further include defining, with respect to path 404, a configuration plan whereby the movable component of manipulator cart 202 is to transform from the initial configuration to the target configuration.

Although FIGS. 3 and 4 have been described with initial and target locations for the manipulator cart 202, the technique described can also be applied to transition from an initial orientation to a target orientation of the manipulator cart 202, and from an initial configuration to a target configuration of the manipulator cart.

Figure 5:
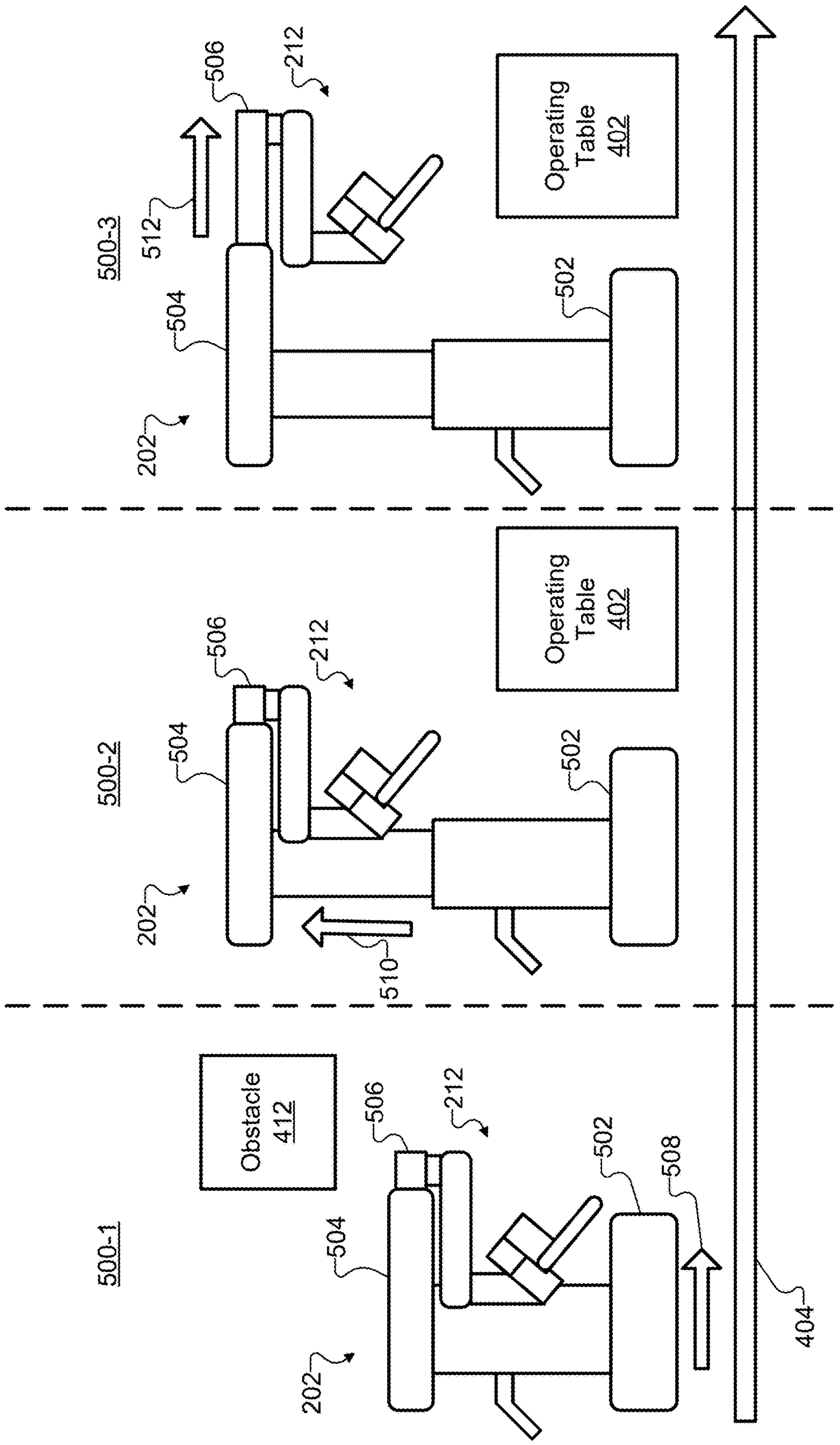
FIGS. 5 and 6 illustrate respective views of the exemplary manipulator cart as the manipulator cart navigates from the initial location and a corresponding initial configuration to the target location and a corresponding target configuration according to principles described herein.
Figure 6:
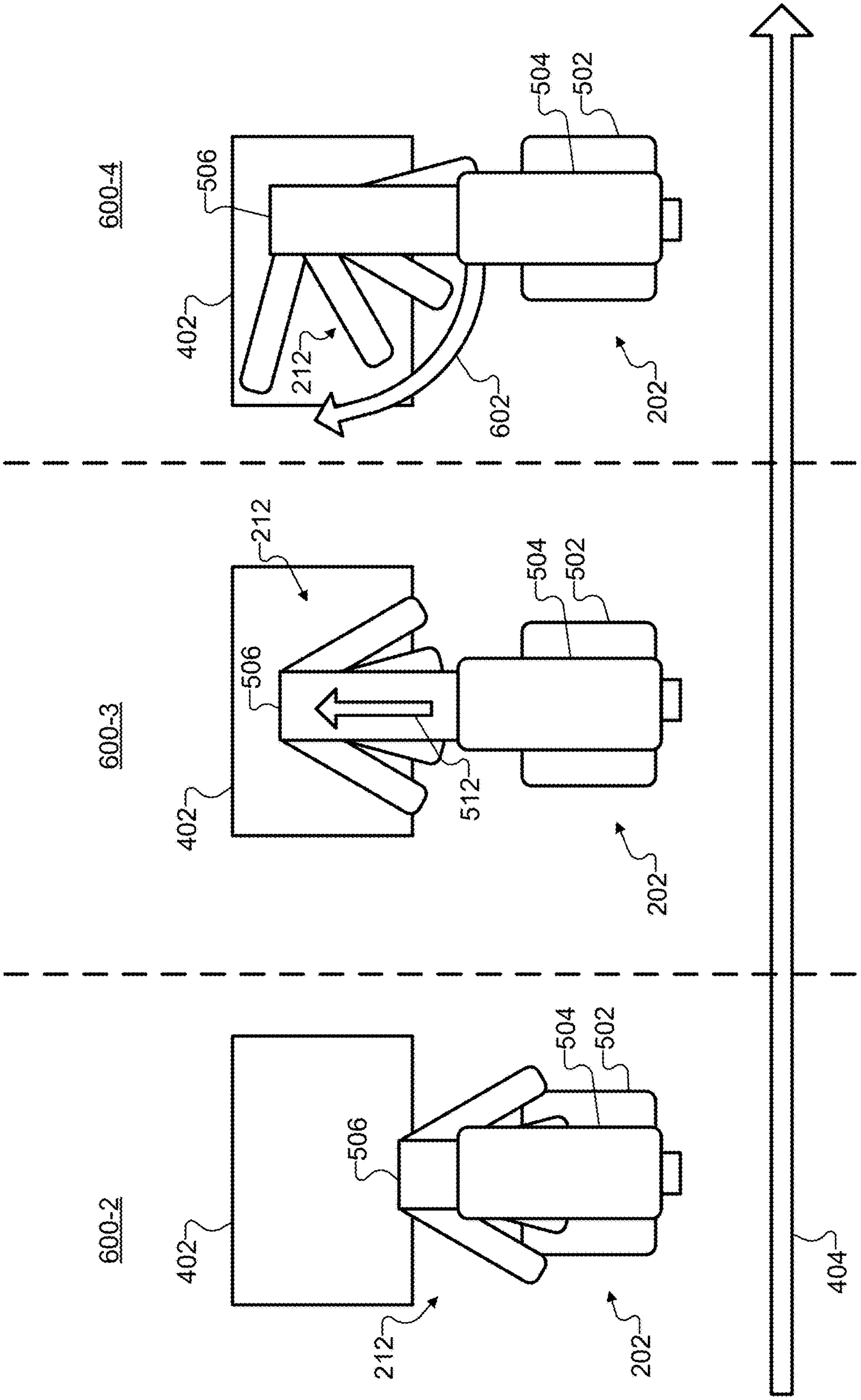

To illustrate, FIGS. 5 and 6 show, respectively, a series of side views and a series of top views of manipulator cart 202 as manipulator cart 202 navigates from location 406-initial and corresponding initial orientation and configuration to location 406-target and corresponding target orientation and configuration associated with path 404. Specifically, as shown in FIG. 5, a series of snapshots 500 (e.g., snapshots 500-1 through 500-3) depict manipulator cart 202 from a side view at three different points in time as manipulator cart 202 traverses path 404. Similarly, as shown in FIG. 6, a series of snapshots 600 (e.g., snapshots 600-2 through 600-4) depict manipulator cart 202 from a top view at three different points in time that will be understood to overlap with the points in time associated with snapshots 500. Specifically, snapshot 600-2 will be understood to depict a top view of manipulator cart 202 at the same point in time depicted by the side view of snapshot 500-2, and snapshot 600-3 will be understood to depict a top view of manipulator cart 202 at the same point in time depicted by the side view of snapshot 500-3.

Various movable components of manipulator cart 202 are labeled in each snapshot 500 and 600. Specifically, manipulator cart 202 is shown to have a base 502 that, when moved across the floor (e.g., driving on wheels or the like that are not explicitly shown), relocates the entire manipulator cart 202. Manipulator cart 202 is further shown to include an operating platform 504 that may be raised and lowered, and to which is attached a boom 506 that may be extended, retracted, pivoted, and so forth. One or more manipulator arms 212 are attached to boom 506 and may each be laterally translated, spread out, brought in, rotated, and/or manipulated in any other manner as may serve a particular implementation. It will be understood that other movable components not explicitly illustrated herein may also be present on manipulator cart 202 or on other manipulator cart implementations.

In some examples, the navigation of base 502 of manipulator cart 202 along path 404 may be planned and performed independently and separately in time from the reconfiguration of other movable components such as operating platform 504, boom 506, and/or arms 212. However, in other examples such as shown in FIGS. 5 and 6, a navigation plan and a configuration plan for manipulator cart 202 may be integrated together such that the navigation of base 502 along path 404 may be performed concurrently with the reconfiguration of the other movable components. In some examples, there may be a seamless and/or integrated transition between navigation control of base 502 and configuration control of other movable components. In certain implementations, these types of control may all be treated the same and may be considered to be part of the navigation along path 404. As such, manipulator cart 202 may not be considered to have completed navigation along path 404 until not only base 502 has arrived at location 406-target and orientated in a target orientation, but also operating platform 504, boom 506, arms 212, and other movable components of manipulator cart 202 have been properly positioned and configured to allow instruments to be connected to arms 212 and docked with cannulas associated with the body on operating table 402. In some instances, no further steps for configuring manipulator cart 202 may be necessary before manipulator cart 202 is ready to begin the medical operation. In other instances, further steps for configuring manipulator cart 202 (e.g., further adjustment of arms 212, adjustment of instruments connected to arms 212, etc.) may be appropriate before manipulator cart 202 is ready to begin the medical operation.

Snapshot 500-1 depicts a lateral movement 508 of base 502 along path 404. Movements such as movement 508 may ultimately result in manipulator cart 202 moving from location 406-initial to location 406-target, as described above. In snapshot 500-1, manipulator cart 202 is shown in an initial configuration that may be associated with a relatively small footprint of manipulator cart 202 (e.g., a minimized amount of space that manipulator cart 202 may take up) in which manipulator cart 202 may be configured when not in use (e.g., when being stored, etc.). As shown, in the initial configuration of snapshot 500-1, operating platform 504 may be completely lowered, boom 506 may be completely retracted, and arms 212 may be tucked away and brought in as much as possible. This initial configuration may be useful for navigating certain parts of path 404. For example, as shown, the initial configuration may allow manipulator cart 202 to pass under overhead obstacle 412 even though, if operating platform 504 were raised somewhat, manipulator cart 202 would not fit under overhead obstacle 412 and obstacle 412 would need to be steered around rather than passed under. Accordingly, path 404 may incorporate and be dependent upon the configuration plan of manipulator cart 202 in the sense that path 404 may be defined to have a requirement that manipulator cart 202 be in a particular configuration (e.g., the initial configuration) when manipulator cart 202 passes under obstacle 412. Analogously, path 404 may incorporate changes in the orientation of manipulator cart 202 to facilitate moving of the manipulator cart 202 to location 406-target.

In snapshots 500-2 (providing a side view) and 600-2 (providing a top view), manipulator cart 202 has arrived at operating table 402 and will be understood to be located at location 406-target such that base 502 has completed all the lateral movements (e.g., movement 508) defined for path 404. At this point in time, it may be desirable for arms 212 to be positioned over operating table 402, but, if manipulator cart 202 is still in the initial configuration of snapshot 500-1, arms 212 would be too low to the ground and would come into contact with operating table 402 if boom 506 were to be extended. Accordingly, as shown in snapshot 500-2, operating platform 504 may be raised by a movement 510 to lift arms 212 above operating table 402.

Thereafter, snapshots 500-3 (providing a side view) and 600-3 (providing a top view) illustrate that boom 506 may now be safely extended by a movement 512 until arms 212 are hovering over operating table 402. For example, boom 506 may be extended until laser crosshairs associated with an arm 212 associated with imaging equipment (e.g., an endoscope) becomes properly aligned with a target cannula that has been inserted into a body (not explicitly shown) on operating table 402. When this alignment is achieved, arms 212 may each be docked to a respective cannula and instruments may be attached to each arm 212 and inserted into the respective cannula. Once each arm 212 is docked with its respective cannula and any further steps to adjust components of manipulator cart 202 or to set up medical system 200 are complete, the medical operation to be performed by medical system 200 may begin.

In certain examples, arms 212 may need to be adjusted (e.g., spread, rotated, reconfigured, etc.) in order to become properly aligned with the cannulas in the manner described above. To illustrate, snapshot 600-4 shows how arms 212 may be spread out from one another and rotated in a movement 602 until each arm is properly aligned and ready for docking with a respective cannula so that the medical operation can begin. Once this final movement is complete, manipulator cart 202 may not only be located at location 406-target, but may also be in the target orientation and/or target configuration associated with the particular medical operation that is to be performed. As such, system 100 may determine and indicate to the operator (e.g., by way of visual, haptic, audible, or any other suitable type of feedback) that the navigation and configuration of manipulator cart 202 is complete.

As mentioned above, reconfiguration of one or more movable components of manipulator cart 202 may be performed separate in time from, or may be integrated with, the movement of base 502 along path 404. For example, in one implementation, the raising of operating platform 504 by movement 510 and the extending of boom 506 by movement 512 may be performed sequentially after movement 508 is complete and base 502 is parked at location 406-target. In other implementations, however, the raising of operating platform 504 by movement 510 and the extending of boom 506 by movement 512 may be performed concurrently with movement 508 and before base 502 has arrived at location 406-target. For example, movement 510 may be initiated as soon as obstacle 412 has been cleared (passed under) and movement 512 may be initiated as soon as operating platform 504 has been raised enough that arms 212 will not come into contact with operating table 402 or a body disposed thereon. In this way, additional valuable time in operating room 400 may be conserved as manipulator cart 202 may be in a location (and orientation and/or configuration, as applicable) even sooner to begin the operation. Moreover, as an additional potential way of conserving time, respective instruments could be attached to arms 212 and docked with cannulas while movement 508 of base 502 is still ongoing in certain examples. The parallelizing of various movements associated with the navigation along path 404 in these ways will be described and illustrated in more detail below with respect to FIGS. 10 and 11.

While implementations have been described above that include both navigation and reconfiguration of movable components of manipulator cart 202, it will be understood that, in certain implementations, system 100 may only be tasked with navigation or reconfiguration of a manipulator cart, and not both. For instance, certain implementations of system 100 may only be configured to assist operators in steering a manipulator cart to a target location, or only configured to assist operators in steering the manipulator cart to a target location and orientation, and users may direct the configuration of other movable components of the manipulator cart without assistance from system 100 once the base of the manipulator cart is in position. As another example, an implementation of system 100 associated with a manipulator system that is, for example, attached bedside to an operating table or that is configured to be moved along a physical track or the like, may not benefit from navigation assistance of system 100. Rather, such a manipulator system may benefit only from assistance of system 100 in configuring movable components such as an operating platform, a boom, and/or manipulating arms.

System 100 may direct manipulator cart 202 to traverse different portions of path 404 in different navigation control modes. For example, as described above, system 100 may direct manipulator cart 202 to navigate along certain portions of path 404 in a bifurcated navigation control mode in which system 100 autonomously controls a steering of manipulator cart 202 while allowing operator control of a propulsion of manipulator cart 202 (e.g., in accordance with a propulsion limitation defined based on an identified navigation condition in certain examples, and not accounting for such a propulsion limitation in other examples). Along other portions of path 404, system 100 may instead direct manipulator cart 202 to navigate in a standard navigation control mode in which system 100 allows operator control of both steering and propulsion of manipulator cart 202.

Figure 7:
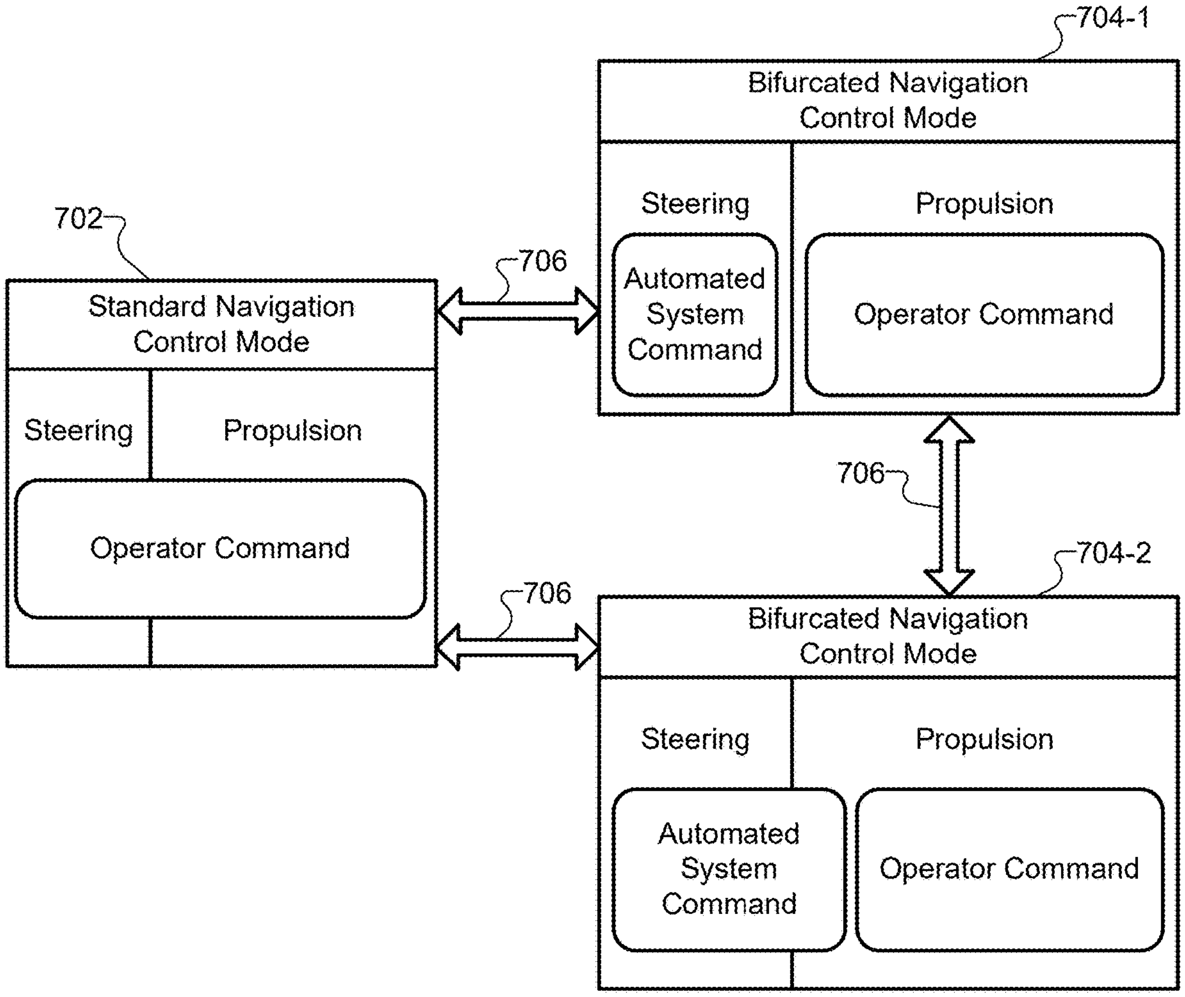
FIG. 7 illustrates various exemplary navigation control modes that may be employed as the manipulator cart navigates from the initial location to the target location according to principles described herein.

To illustrate, FIG. 7 shows various exemplary navigation control modes that may be employed as manipulator cart 202 navigates from location 406-initial (and a corresponding initial orientation and/or a corresponding initial configuration) to location 406-target (and a corresponding target orientation and/or a corresponding target configuration). Specifically, FIG. 7 shows representations of a standard navigation control mode 702 and two different bifurcated navigation control modes 704 (bifurcated navigation control modes 704-1 and 704-2). In each navigation control mode representation depicted in FIG. 7, an indication is given of who or what commands the steering and the propulsion of manipulator cart 202 by labels indicating "Automated System Command" (i.e., automatically commanded by system 100) or "Operator Command" (i.e., commanded by a human operator) being placed, as appropriate, in columns for "Steering" and "Propulsion". The entity indicated to command the steering determines which direction the manipulator cart will go when moved. The entity (or entities) indicated to command the propulsion determines the movement, speed, and acceleration of the manipulator cart, whether in a forward direction (positive speed), a backward direction (negative speed), or remaining at a standstill (zero speed).

As shown, standard navigation control mode 702 is characterized by the operator dynamically commanding both the steering and the propulsion of manipulator cart 202. In contrast, bifurcated navigation control modes 704-1 and 704-2 are both characterized by bifurcating the steering and propulsion control in different ways, each allowing operator control of some or all aspects of the propulsion while the steering is controlled by system 100 automatically. It will be understood that other navigation control modes not explicitly shown (e.g., a navigation control mode providing automated system command of the steering and the magnitude of the speed while allowing operator command of whether the manipulator cart moves at a positive (i.e., forward), negative (i.e., backward) or zero speed) may also be employed in certain examples.

The differences between bifurcated navigation control modes 704-1 and 704-2 include the extent to which the system is involved in propulsion control. FIG. 7 shows that in bifurcated navigation control mode 704-1, the steering of manipulator cart 202 is entirely under automated system command, while the propulsion of manipulator cart 202 is entirely operator commanded. Accordingly, it will be understood that, in bifurcated navigation control mode 704-1, system 100 may be configured to automatically control the steering, and to not impose any propulsion limitations on the propulsion based on navigation conditions. A bifurcated navigation system may or may not implement navigation control mode 704-1. In systems that do implement navigation control mode 704-1, mode 704-1 may be the only bifurcated navigation control mode available, or may be one of a plurality of bifurcated navigation control modes available. Where mode 704-1 is one of a plurality of bifurcated navigation control modes available, as shown in FIG. 7, it may be active in response to being a default control mode when the system enters into bifurcated navigation, to one or more navigation conditions indicating no propulsion limitations are applicable, to the operator indicating that he or she wishes to have full propulsion control without system-imposed limitations, etc.

In bifurcated navigation control mode 704-2, the steering of manipulator cart 202 is entirely under automated system command, while the propulsion (e.g., forward or backward speed along path 404, remaining stopped on path 404, etc.) is controlled by a human operator with one or more propulsion limitations imposed by system 100. This is illustrated in FIG. 7 by the Propulsion column overlapping with both "Automated System Command" and "Operator Command." As a specific example, the control interface described above in relation to bifurcated navigation control mode 704-2 may be configured to detect an operator's selection of a speed, onto which a system-imposed propulsion limitation is applied; the system and the operator therefore both contribute to the propulsion control. For example, as will be described in more detail below, the operator may control the speed of manipulator cart within system-imposed propulsion limits such as maximum or minimum speed limits, maximum or minimum acceleration limits, etc. In some examples, the operator's selection of the propulsion may be from a plurality of distinct propulsion settings (e.g. a plurality of discrete speed settings). In other examples, the operator's selection of the propulsion may be from a continuous spectrum of potential propulsion settings (e.g. an analog input allowing an infinite number of speed settings). Both discrete and continuous propulsion may be based on an input associated with an amount of exertion (e.g., amount and/or direction of force or torque) applied by the operator to command movement of the manipulator cart 202.

Various transitions 706 between navigation control modes 702 and 704 are shown in FIG. 7 to illustrate that the system may transition between navigation control modes 702 and 704 in any suitable way and for any suitable reason as may serve a particular implementation. For example, certain implementations may support all of the navigation control modes 702, 704-1, and 704-2 shown in FIG. 7, and during operation may transition from mode to mode as the operator or navigation conditions may dictate. As described above, certain implementations may not include bifurcated navigation control mode 704-1, in which case the system may transition between modes 702 and 704-2 as appropriate. Further, certain implementations may not include navigation control modes 702 and 704-1.

Before system 100 may operate in a navigation control mode (e.g. mode 702, 704-1, or 704-2) where manipulator cart 202 can begin to navigate or move at all, system 100 may monitor for certain criteria being met. For instance, in certain examples, manipulator cart 202 is first determined to be navigable (e.g., based on one or more criteria such as powered on, able to be moved, not have parking feet deployed, have powered drive operational, not have brakes engaged, and so forth). In some implementations, system 100 determines navigability further based on indications of stage of medical procedure (e.g. to not have any arm 212 attached to a cannula or instrument). Once manipulator cart 202 is determined to be navigable, system 100 may check for additional criteria to determine whether any of bifurcated navigation control modes 704 (or a single bifurcated navigation control mode 704-1 or 704-2 if the system supports only one bifurcated navigation control mode) are to be made available for use. For example, system 100 may determine one or more of: if manipulator cart 202 is in a stowed position (e.g., such as shown above in snapshot 500-1 of FIG. 5), if a suitable path from an initial location to a target location (and, as applicable, from an initial orientation or configuration to a target orientation or configuration) can be defined, or the like.

In some examples, the entire path (e.g., path 404) may be defined before manipulator cart 202 begins to traverse the path. In other examples (as described above), however, the entire path (e.g., path 404) may not be defined from the outset before manipulator cart 202 begins to traverse the path (i.e., because the path may be defined and updated dynamically as manipulator cart 202 is moving along the path). If sensors used for pathfinding are blocked, or system 100 determines that no suitable path exists (e.g., because no path actually does exist, because a path cannot be found, because paths that are found are too complex or narrow, etc.), system 100 may determine (and indicate to the operator through visual, audible, haptic, or other suitable cues) that no bifurcated navigation control mode is currently to be made available, and apply the standard navigation control mode.

If system 100 determines that a bifurcated navigation control mode 704 is available for use, it may be desirable for manipulator cart 202 to navigate the entirety of path 404 in a single bifurcated navigation control mode (e.g. control mode 704-1 or 704-2), or while switching between bifurcated navigation control modes 704 (e.g., in bifurcated navigation control mode 704-1 when navigation conditions do not call for any propulsion limitation, and in bifurcated navigation control mode 704-2 when such a propulsion limitation is appropriate in light of the navigation conditions). However, in certain situations, particular conditions or events may cause system 100 to make the bifurcated navigation control modes 704 unavailable during the navigation, such that system 100 switches out of any active bifurcated navigation control mode 704. For example, system 100 may switch from one of bifurcated navigation control modes 704 to standard navigation control mode 702 in order to allow operator control of both the steering and the propulsion of the manipulator cart in response to pathfinding issues. Once any pathfinding issues are resolved (e.g., once obstacles have been cleared, once the target location is identified or re-acquired, once a valid path can be determined, etc.) and/or once an operator so indicates, system 100 may transition from standard navigation control mode 702 back to an appropriate one of bifurcated navigation control modes 704.

In some examples, system 100 may be configured to exit bifurcated navigation in response to operator input. For example, system 100 may receive, while in one of bifurcated navigation control modes 704, operator input resisting autonomous steering of the manipulator cart. For example, the operator input may be received at the control interface by the operator exerting a force on the control interface that opposes the steering control that system 100 is performing. In other examples, operator input may not involve physically resisting the system steering control, but instead may involve the pressing of a button or switch, the ceasing of pressing a button or switch, or the selection of another suitable user input mechanism by the operator. In response to any such operator input, system 100 may transition from directing the navigation along the path in the bifurcated navigation control mode 704 to allowing the navigation along the path in standard navigation control mode 702. System 100 may also indicate to the operator (e.g., using a haptic rumble or any other feedback cue described herein) that the navigation control mode has been changed.

In other examples, the switching to standard navigation control mode 702 from the bifurcated navigation control mode 704 may be based on conditions other than explicit user input. For example, system 100 may identify a navigation condition associated with the navigation of manipulator cart 202 along path 404, and, based on the navigation condition, may transition (and indicate the transition to the operator) from directing the navigation along path 404 in one of bifurcated navigation control modes 704 to allowing the navigation along path 404 in standard navigation control mode 702.

The navigation condition identified may be any of various conditions and/or events that system 100 may detect, and may be the same, similar, or different from navigation conditions discussed below that may be the basis for defining propulsion limitations. For example, one navigation condition that may be determined to initiate a switch from one of bifurcated navigation control modes 704 to standard navigation control mode 702 may be that operating table 402 is detected to have moved from its prior location, thus necessitating a recalculating of location 406-target and path 404. Other navigation conditions may include that a battery of manipulator cart 202 is detected to be low or fully exhausted, that manipulator cart 202 or a component thereof is detected to be out of place (e.g., arms 212 splayed too widely) or to not be functioning properly, that manipulator cart 202 has not been fully sterilized (e.g., draped) and is hence not prepared to be placed in the sterile field for the operation, or the like. In still other examples where path 404 is being defined dynamically as manipulator cart 202 is navigating along the path, a navigation condition initiating a return to standard navigation control mode 702 may be that path 404 is detected to become unnavigable, system 100 fails to find the next portion of path 404, sensor line-of-sight to location 406-target is lost (e.g., because sensors are blocked, etc.), or the like. In yet another example, detection of general motion of obstacles and other objects within operating room 400 may cause system 100 to decrease a confidence level of a previously-defined path until it is determined that the path must be redefined. For instance, system 100 may measure the amount of entropy in operating room 400, the level of activity in operating room 400, or the like, and determine, based on that measurement, whether to proceed in a bifurcated navigation control mode 704 or to require navigation to proceed in standard navigation control mode 702 so that a human operator can determine how best to deal with the complexity.

While FIG. 7 does not explicitly indicate how an operator is to provide operator commands, it will be understood that such commands may be input by way of any control interface as may serve a particular implementation. For instance, in certain implementations or for certain portions of the navigation, a primary control interface may be used such as a handlebar-based control interface integrated into manipulator cart 202, or one or more other suitable control mechanisms (e.g., a steering wheel, a joystick, a touch screen control panel, a remote control, a throttle, one or more buttons or switches, etc.). In other implementations or for other portions of the navigation, a secondary or auxiliary control interface that is distinct and separate from the primary control interface may be used. For example, a secondary control interface may be employed that is suitable and convenient for use in a bifurcated navigation control mode such as one of bifurcated navigation control modes 704, but that might not be suitable for use in standard navigation control mode 702 because the secondary control interface is not as well-suited to facilitate operator control of steering of manipulator cart 202. For instance, exemplary secondary control interfaces may include gesture-based control interfaces, voice-controlled interfaces, manipulator arm-guided interfaces (e.g., in which an operator guides manipulator cart 202 by pulling or pushing on a particular manipulator arm 212), separate input devices such as separate joysticks or control pads, or the like. While certain secondary control interfaces may not be well-suited to facilitate operator control of steering, other secondary control interfaces may be configured to facilitate operator control of both the propulsion and the steering of the manipulator cart, but may be auxiliary to the primary control interface by otherwise including fewer features than the primary control interface, by being used from an opposite side of the manipulator cart than the primary control interface, or in other suitable ways. For example, certain such secondary control interfaces may be configured to be used by an operator in a sterile environment (e.g., an operator located in a sterile field on a patient side of the manipulator cart, rather than located in a non-sterile field on the opposite side of the manipulator cart).

Figure 8:
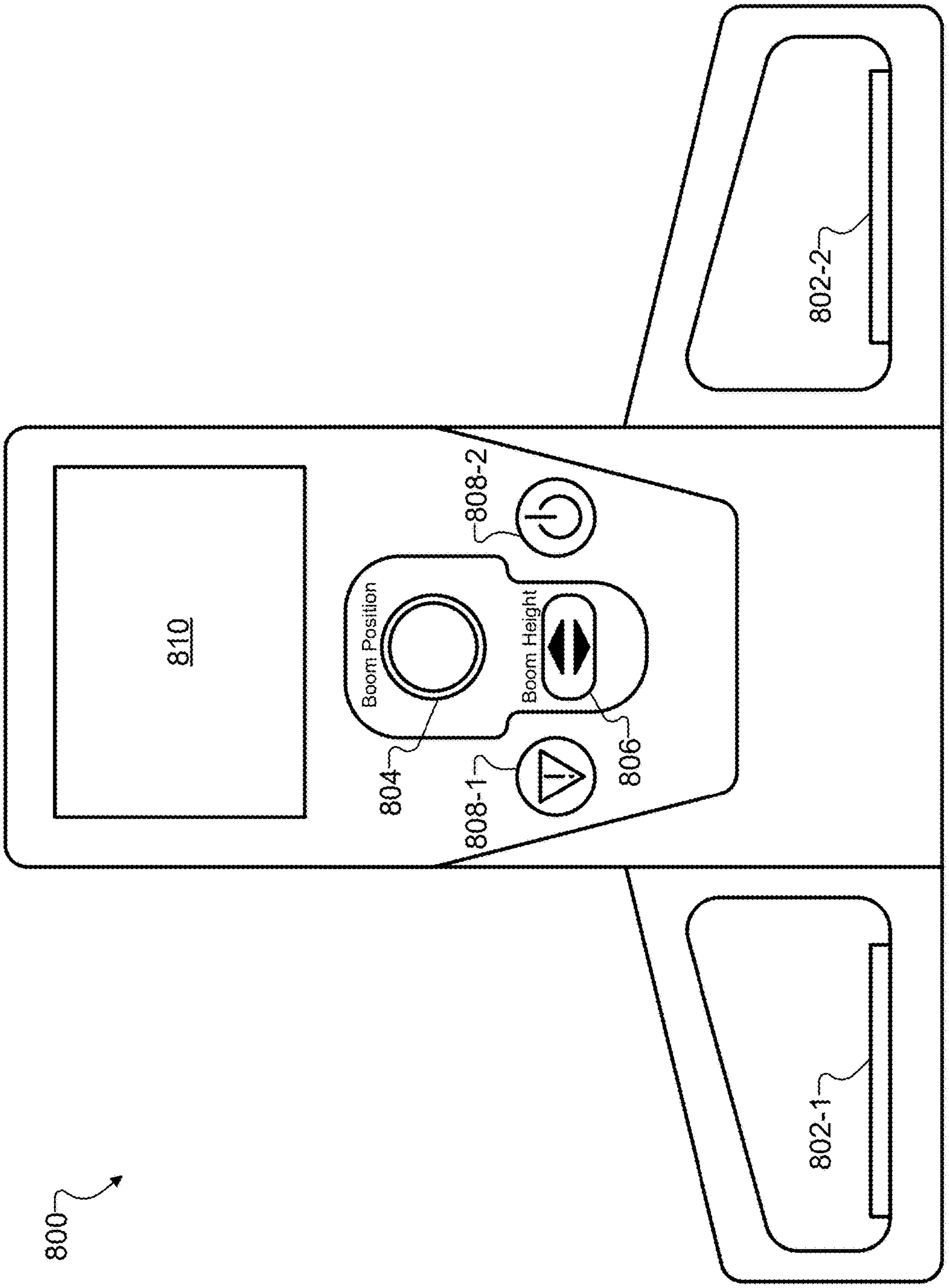
FIG. 8 illustrates exemplary components of a control interface that may be employed during navigation of the manipulator cart from the initial location to the target location according to principles described herein.

FIG. 8 illustrates exemplary components of a control interface that may be employed during navigation of manipulator cart 202 from location 406-initial to location 406-target. Specifically, FIG. 8 illustrates a control interface 800 implemented as a handlebar-based primary control interface. As shown, control interface 800 is implemented as a handlebar-based control interface integrated into manipulator cart 202 (i.e., built into manipulator cart 202 such as on the opposite side of manipulator cart 202 from arms 212). FIG. 8 shows various controls that may be included in control interface 800 in a particular implementation. Specifically, control interface 800 is shown to include drive switches 802 (i.e., drive switches 802-1 and 802-2) built into handlebars that allow an operator to conveniently steer and/or direct propulsion of manipulator cart 202. For example, in standard navigation control mode 702, one or both of drive switches 802 may be pressed to cause manipulator cart 202 to drive forward, and turns may be directed by the user pulling or pushing the handlebars to one side or the other. The handlebars and drive switches 802 may thus be used to steer and direct propulsion of manipulator cart 202 along a path such as path 404.

Other controls included within control interface 800 may facilitate operator-guided movement of other movable components of manipulator cart 202. For example, control interface 800 includes a boom position knob 804 that may be pushed forward to extend boom 506 (e.g., such as illustrated by movement 512), pulled backwards to retract boom 506, pushed left or right to pivot boom 506, or turned clockwise or counterclockwise to rotate arms 212 on boom 506 (e.g., such as illustrated by movement 602). As another example, control interface 800 is shown to include a boom height rocker switch 806 that, when pushed forward may raise operating platform 504 (e.g., such as illustrated by movement 510), and when pulled backward may lower operating platform 504. Additionally, as further shown, control interface 800 may include various buttons 808 (e.g., buttons 808-1 and 808-2) used to input an emergency stop command (button 808-1), to power on and off manipulator cart 202 (button 808-2), or to perform other operations as may serve a particular implementation. While a few specific input controls are explicitly shown in FIG. 8 for illustration, it will be understood that more or fewer controls that perform similar or different functionality as described above may be included on other implementations of control interface 800.

Along with the controls described above, control interface 800 is shown to further include a touchscreen 810 used to accept other types of input commands (e.g., based on user selection of touchscreen panels) and to provide output information to the operator. Specifically, touchscreen 810 may provide visual feedback to the operator, while other suitable output mechanisms such as loudspeakers, actuators, LEDs, buzzers, etc., may be used to provide visual and/or other types of feedback (e.g., audible feedback, haptic feedback, etc.). It will be understood that, in certain examples, touchscreen 810 may not include a touch panel, but, rather, may be implemented only as a display monitor capable of outputting information and not accepting operator input. In still other examples, control interface 800 may be implemented exclusively by buttons, knobs, and/or other controls, and may not include any display monitor or touch screen.

Various types of feedback may be provided to an operator by way of touchscreen 810 and/or other output mechanisms of control interface 800. For example, system 100 may provide, to an operator performing operator control of manipulator cart 202 by way of control interface 800, one or more status indicators. For example, the status indicators may indicate a progression of manipulator cart 202 along path 404, whether manipulator cart 202 has completed navigating path 404, details about any propulsion limitation being imposed on the propulsion of manipulator cart 202, and so forth. The status indicators may take any form as may serve a particular implementation. For example, one status indicator may indicate what percentage of path 404 has been traversed and indicate when manipulator cart 202 arrives at location 406-target (as well as at a target orientation and/or configuration, if applicable) and/or completes path 404. As another example, another status indicator may show (e.g., from a top view) a depiction of path 404 (e.g., including locations 406-initial and 406-target, obstacles 410 and/or 412, etc.) so as to indicate a current location of manipulator cart 202 on path 404. In some examples, after manipulator cart 202 has arrived at location 406-target and has stopped, the status indicator may continue to indicate that manipulator cart 202 has not completed navigating path 404 until a target orientation has been achieved and/or until each movable component has been properly configured according to the configuration plan.

Other types of feedback provided by way of control interface 800 may include a current position of manipulator cart 202 shown on a map of path 404 (e.g., a map indicating turns, obstacles shown in different colors, etc.), an indication that navigation has stopped short, an indication that navigation has been attempted to continue forward after navigation was complete, and/or 2D photographic imagery or 3D model imagery captured by or derived from sensors on manipulator cart 202 (e.g., imagery depicting ports and/or cannulas being approached). Moreover, control interface 800 may provide feedback when system 100 switches between a dynamically-generated path and a full pre-defined path (e.g., when location 406-target is identified and a path all the way to location 406-target and/or to a final target configuration is defined), when control switches from one bifurcated navigation control mode to another, or when the navigation control mode switches (e.g., from the standard navigation control mode to a bifurcated navigation control mode, from one bifurcated navigation control mode to another, etc.). As another example, control interface 800 may provide feedback showing regions where manipulator cart 202 may park (e.g., a target location or a range of potential target locations), feedback indicating a range of motion of various movable components of manipulator cart 202, an indication of when sterile field 408 has been entered by manipulator cart 202, an indication of which navigation control mode is currently in use, and/or an indication of which direction manipulator cart 202 is moving or is supposed to be moving according to path 404. With regard to indicating the propulsion limitation, control interface 800 may provide feedback indicative of a current speed of manipulator cart 202, a top speed of manipulator cart 202 (e.g., if a maximum speed limit for manipulator cart 202 is imposed as a propulsion limitation), a difference between the top speed and the current speed, an indication of the speed gain (e.g., as described below in more detail), and so forth.

Haptic or other feedback may also be provided to operators of manipulator cart 202. For instance, rather that providing visual feedback by way of touchscreen 810, system 100 may use boom 506, arms 212, or another such component of manipulator cart 202 to, for example, point in the direction that manipulator cart 202 is currently steering. It will be understood that certain of the types of feedback described above may be provided in one or more ways other than the ways explicitly described herein (e.g., visually, audibly, haptically, etc.). Additionally, it will be understood that certain types of feedback described above may be provided not only by control interface 800, but also by other types of control interfaces described herein (e.g., other primary control interfaces, secondary control interfaces, etc.).

Regardless of which type of control interface is employed in a particular implementation or along a particular segment of path 404, propulsion control of manipulator cart 202 may be influenced by both an operator and system 100 whenever navigation proceeds in bifurcated navigation control mode 704-2. To illustrate how this joint effort between the operator and the system may function, FIG. 9 shows exemplary factors that may be accounted for in the propulsion of manipulator cart 202 in bifurcated navigation control modes 704.

Specifically, as shown, an operator 902 may provide user input indicative of various propulsion characteristics (e.g., speed, acceleration, etc.) selected by operator 902 for manipulator cart 202. This user input is shown in FIG. 9 as operator-commanded propulsion 904 and may be provided by operator 902 in any suitable way (e.g., by a magnitude of the exertion operator 902 is delivering to push or pull manipulator cart 202—such as a magnitude of a force or torque applied by operator 902, by a degree to which operator 902 is partially or fully engaging a throttling mechanism configured to control the speed of manipulator cart 202, by a continuous or discrete speed level selected by operator 902, etc.). System 100 is also shown to account for one or more navigation conditions 906, which may be detected in various ways and may include various types of conditions that will be described in more detail below.

As shown, system 100 may input both operator-commanded propulsion 904 and navigation conditions 906, and may further manage one or more propulsion limitations 908. Using propulsion limitations 908, system 100 may determine how operator-commanded propulsion 904 is to be translated into actual propulsion of manipulator cart 202, labeled in FIG. 9 as manipulator cart propulsion 910. For example, as will be described in more detail below, system 100 may determine that manipulator cart propulsion 910 should be exactly the same as operator-commanded propulsion 904 for certain navigation conditions 906, and may determine that propulsion limitations 908 should be used to adjust operator-commanded propulsion 904 to a more appropriate or desirable manipulator cart propulsion 910 for other navigation conditions 906. In either case, system 100 may use one or more propulsion control signals 912 to implement whatever manipulator cart propulsion 910 is deemed to be appropriate (e.g., whether it is exactly what operator 902 commands or a limited version thereof). For example, propulsion control signals 912 may represent voltage or power signals delivered to actuators associated with a drive mechanism of manipulator cart 202. As another example, propulsion control signals 912 may include data instructions or the like that indicate to an onboard drive controller of manipulator cart how such actuators are to be directed.

Figure 9:
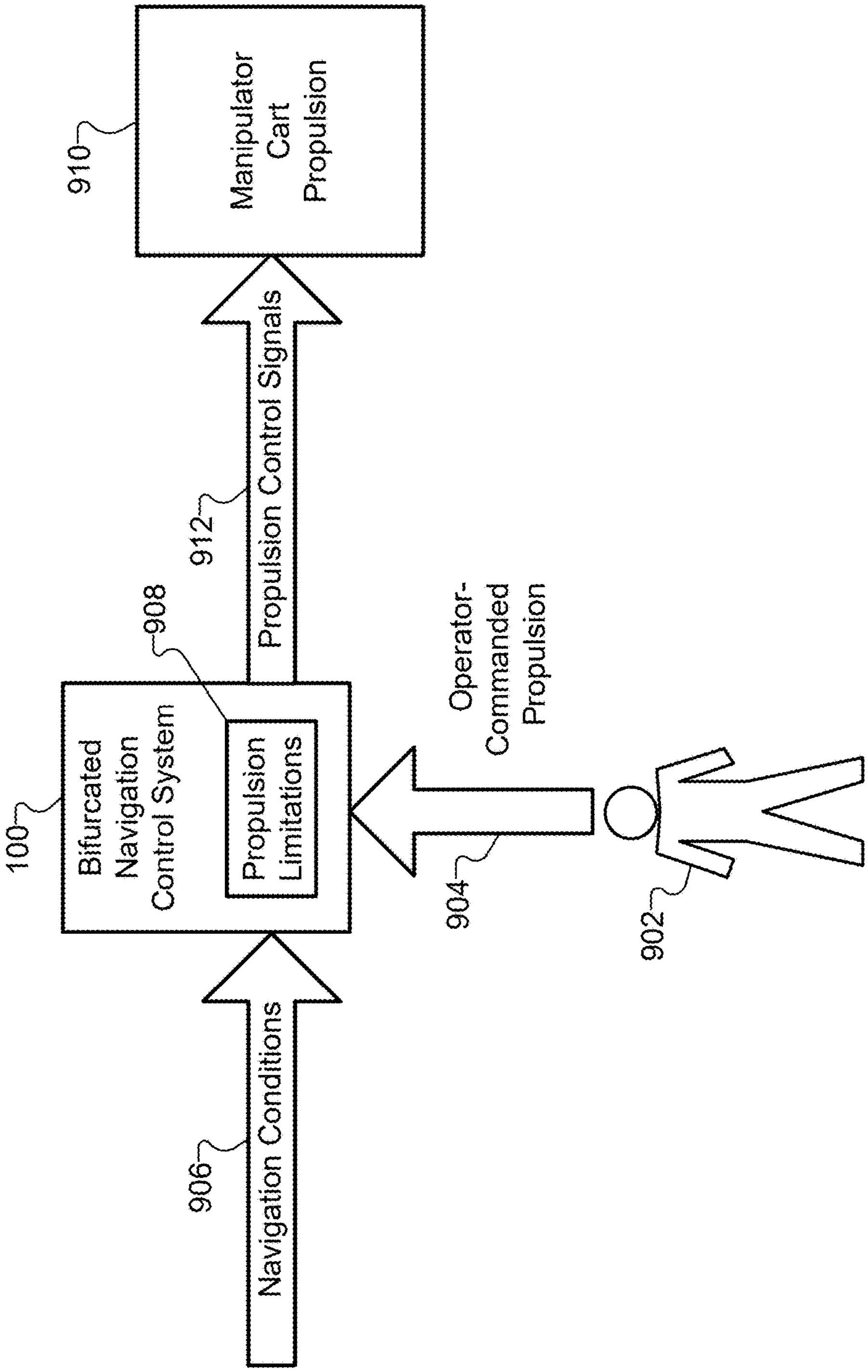
FIG. 9 illustrates exemplary factors accounted for in the propulsion of the manipulator cart in certain navigation control modes of FIG. 7 according to principles described herein.

In FIG. 9, manipulator cart propulsion 910 may refer to any suitable propulsion characteristics associated with any type of advancement of manipulator cart 202 along a path (e.g., path 404) or in relation to a configuration plan as may serve a particular implementation. For example, manipulator cart propulsion 910 may include movement of base 502 along path 404, reconfiguration of movable components (e.g., operating platform 504, boom 506, arms 212, etc.) in accordance with a configuration plan, or any other advancement toward a final position and configuration in which manipulator cart 202 will be ready to perform the operation. As such, it will be understood that FIG. 9 illustrates what has been described herein as system 100 directing manipulator cart 202 to navigate along a part of path 404 in a bifurcated navigation control mode in which system 100 allows operator control of a propulsion of manipulator cart 202 (i.e., operator-commanded propulsion 904) in accordance with a propulsion limitation (e.g., one of propulsion limitations 908).

Operator-commanded propulsion 904 may refer to any operator input as may be provided by an operator 902 and/or as may be accounted for by an implementation of system 100. For example, in certain implementations or along certain portions of path 404 being navigated, operator-commanded propulsion 904 may provide directional propulsion commands such as forward propulsion commands, backwards propulsion commands, and stop propulsion commands, as well as operator selected speed settings, specific commands to proceed with a configuration plan whereby moveable components of manipulator cart 202 are transformed from an initial configuration to a target configuration, and/or other commands as may serve a particular implementation. As described above, in these examples, manipulator cart propulsion 910 may be said to be controlled in one of bifurcated navigation control modes 704. Operator-commanded propulsion 904 may be provided by operator 902 in any manner and by way of any control interface as may serve a particular implementation (e.g., including by way of control interface 800).

Figure 10:
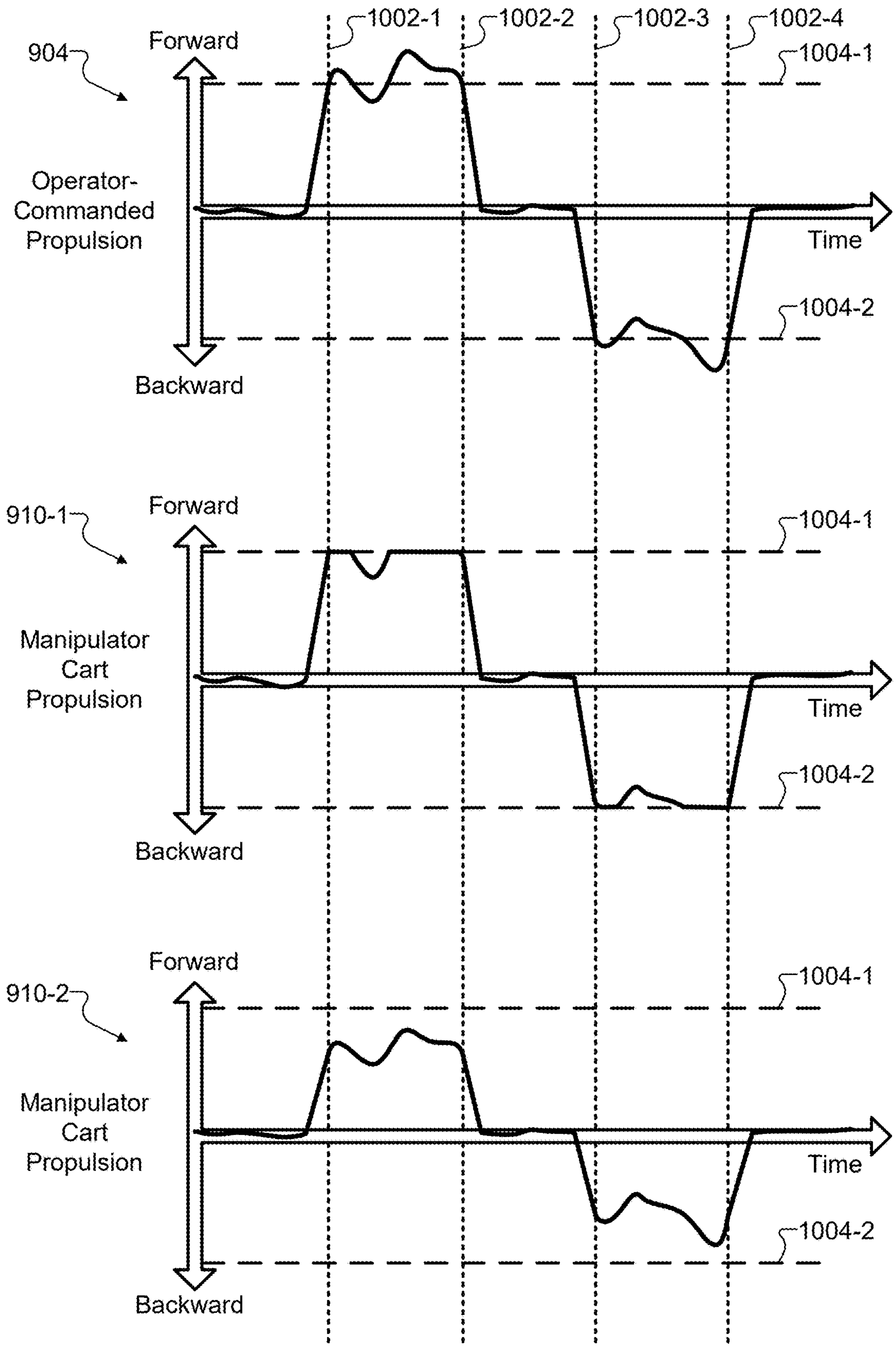
FIG. 10 illustrates how exemplary operator-commanded propulsion may be translated into manipulator cart propulsion in accordance with different types of propulsion limitations and with respect to time according to principles described herein.

As operator 902 provides operator-commanded propulsion 904, one or more propulsion limitations 908 may influence how operator-commanded propulsion 904 is used to ultimately control manipulator cart propulsion 910. To illustrate, FIGS. 10-12 depict various examples of how operator-commanded propulsion 904 may be translated into manipulator cart propulsion 910 in accordance with different types of propulsion limitations 908 that may be used individually or in combination with one another in various implementations or under various navigational circumstances and conditions. Each of these figures will now be described in more detail.

FIG. 10 illustrates different ways that exemplary operator-commanded propulsion 904 may be translated into manipulator cart propulsion 910 (e.g., manipulator cart propulsion 910-1 or 910-2 in different examples) in accordance with different types of propulsion limitations 908. Specifically, FIG. 10 includes three graphs: a top graph that is representative of exemplary operator-commanded propulsion 904 and middle and bottom graphs that are each representative of manipulator cart propulsion that may result from different propulsion limitations 908. Each of the graphs shown in FIG. 10 represents a propulsion characteristic such as speed or acceleration on the y-axis, where positive values represent propulsion values in a forward direction along path 404 and negative values represent propulsion values in a backward direction along path 404. Each of the graphs also shows time along the x-axis.

As shown, each graph indicates certain reference values that will be understood to be the same values from graph to graph. Specifically, dotted lines labeled as times 1002 (i.e., times 1002-1 through 1002-4) represent the same points in time for each of the graphs, while dashed lines labeled as reference levels 1004 (e.g., reference levels 1004-1 and 1004-2) represent the same propulsion levels (e.g., the same speeds, the same accelerations, etc.) for each of the graphs.

FIG. 10 illustrates that operator-commanded propulsion 904 may begin with a zero propulsion command (i.e., no command to move manipulator cart 202, or a command to stop manipulator cart 202) until about time 1002-1. Around time 1002-1, operator-commanded propulsion 904 is shown to move up to about reference level 1004-1, where the operator-commanded propulsion 904 hovers just over or just under this propulsion level until about time 1002-2. At this point, operator-commanded propulsion 904 returns to a level around zero, such that operator-commanded propulsion 904 may be interpreted as another zero propulsion command until about time 1002-3. Then, starting around time 1002-3, operator-commanded propulsion 904 moves down to about reference level 1004-2, where operator-commanded propulsion 904 hovers just over or just under this propulsion level until about time 1002-4, after which operator-commanded propulsion 904 returns to the zero level.

System 100 may translate this operator-commanded propulsion 904 into manipulator cart propulsion 910 in various ways based on different propulsion limitations 908. For example, as illustrated by manipulator cart propulsion 910-1 in the middle graph, one exemplary propulsion limitation 908 may impose an upper propulsion limit (e.g., a maximum speed limit, a maximum acceleration limit, etc.) on manipulator cart 202. System 100 does not modify the operator-commanded propulsion based on this type of propulsion limitation as long as the operator-selected propulsion value (e.g., an operator-selected speed setting, an operator-selected acceleration rate, etc.) satisfies the limit (e.g. remains below a certain level—in this case below reference level 1004-1 in the forward direction, or below reference level 1004-2 in the backward direction). However, the propulsion value is shown to become saturated at the maximum limit such that operator 902 is not given the ability to direct manipulator cart 202 to accelerate faster or move at any speed above the maximum propulsion limit at reference levels 1004-1 and 1004-2. In this example, system 100 achieves this result by modifying operator-commanded propulsion exceeding the propulsion limit to be equal to the propulsion limit.

The maximum propulsion limit may be defined, or may be set at any propulsion level (e.g., speed, acceleration rate, etc.) as may serve a particular implementation. For example, system 100 may define the maximum propulsion limit as applicable to the navigation, or define the value of the maximum propulsion limit, or define both the applicability or the value, based on a proximity of manipulator cart 202 to an obstacle to be avoided by manipulator cart 202 during the navigation of manipulator cart 202 along the path (e.g., one of obstacles 410 or 412 during the navigation along path 404). As a specific example, system 100 may define the propulsion limitation by determining to apply the maximum propulsion limit or not based on parameter(s) such as the distance of manipulator cart 202 to the obstacle being within a threshold distance; in such an implementation, the value of the maximum propulsion limit may be statically set, or dynamically calculated based on one or more navigation conditions. As another specific example, system 100 may define the propulsion limitation by determining the value of the maximum propulsion limit based the distance of manipulator cart 202 to the obstacle; in such an implementation, the value of the maximum propulsion limit may be lower when the distance of manipulator cart 202 to the obstacle is lower, and higher when the distance of manipulator cart 202 to the obstacle is higher. As a further example, system 100 may define the propulsion limitation by both determining if to apply the maximum propulsion limit, and determining the value of the maximum propulsion limit. As yet another example, system 100 may define the propulsion limitation by determining which operator control interface is to be used (e.g., a primary control interface, a secondary control interface, etc.) to provide propulsion commands.

Moreover, the maximum propulsion limit may be defined, or further defined, based on a predetermined deceleration rate of manipulator cart 202, such that there is sufficient time for manipulator cart 202 to slow to a safe speed, or to a stop, before colliding with the obstacle if necessary. As another example, if manipulator cart 202 comprises one or more movable components (e.g., operating platform 504, boom 506, arms 212, etc.), system 100 may define the maximum propulsion limit based on a proximity of manipulator cart 202 to an obstacle to be avoided by the movable component during the navigation of manipulator cart 202 along the path, an orientation of the movable component with respect to the obstacle, and a movement rate of the movable component. The maximum propulsion limit may thus be selected so as to allow sufficient time for the movable component of manipulator cart 202 to be reconfigured, prior to manipulator cart 202 reaching the obstacle at a current approach trajectory, in order to avoid the obstacle. For example, system 100 may determine that a collision with obstacle 412 may be avoided by lower operating platform 504 to pass under obstacle 412, as was illustrated above in FIG. 5. Similarly, system 100 may also determine that a collision with operating table 402 may be avoided by raising operating platform 402. Accordingly, the maximum propulsion limit for manipulator cart 202 may be defined in such a way as to give operating platform 504 enough time to be lowered and then to be raised in order to avoid these collisions. In some examples (e.g., when obstacles are in motion or when various other conditions exist), system 100 may dynamically define the maximum propulsion limit based on navigation conditions, and the maximum propulsion limit may therefore be a variable, rather than a fixed, value.

As shown in the middle graph, manipulator cart propulsion 910-1 generally follows operator-commanded propulsion 904 except when operator-commanded propulsion 904 goes outside of the propulsion levels 1004-1 and 1004-2 (i.e., except when accelerating or moving faster than the values represented by propulsion levels 1004). At these times, FIG. 10 shows that manipulator cart propulsion 910-1 saturates so as to not accelerate at a higher rate, or move at a higher speed, than the propulsion limits set at propulsion levels 1004-1 and 1004-2. For example, manipulator cart propulsion 910-1 may saturate to limit the acceleration or speed of the base of manipulator cart 202 along path 404. Additionally or alternatively, manipulator cart 910-1 may limit the acceleration or speed of other movable components of manipulator cart 202 such as the boom, the operating platform, or the like. In this way, system 100 allows operator 902 to exert propulsion control on manipulator cart 202 while still ensuring that manipulator cart propulsion 910-1 does not exceed an appropriate propulsion level even if so commanded by operator 902.

System 100 may also impose other types of propulsion limitations 908 on the operator-controlled propulsion of manipulator cart 202 (i.e., propulsion limitations other than upper limits). For example, as shown by manipulator cart propulsion 910-2 in the bottom graph, another exemplary propulsion limitation 908 may define, act as, or be thought of as, a transfer function or gain control for converting one or more aspects of operator-commanded propulsion 904 (e.g., a commanded speed setting, a commanded acceleration rate, etc.) into a different but corresponding manipulator cart propulsion 910-2 (e.g., a reduced percentage such as half of operator-commanded propulsion 904, a set amount lower than operator-commanded propulsion 904, etc.). For example, this type of propulsion limitation may include a mapping of input exertion applied to the operator control (e.g., operator-commanded propulsion 904 implemented as how hard a user pushes the operator control) to a speed or an acceleration of manipulator cart 202 (e.g., manipulator cart propulsion 910). As another example, this type of propulsion limitation may include a designated speed gain associated with a speed control interface of the manipulator cart, and system 100 direct (e.g., by way of propulsion control signals 912) the propulsion of manipulator cart 202 to be performed at a speed determined by an operator-selected speed setting for the speed control interface.

As shown in the bottom graph of FIG. 10, manipulator cart propulsion 910-2 follows the shape of operator-commanded propulsion 904 but does not match the amplitude of operator-commanded propulsion 904. For example, manipulator cart propulsion 910-2 may consistently be directed at a particular percentage (e.g., about 60% in this example) of operator-commanded propulsion 904. In this example, the manipulator cart propulsion can exceed levels 1004-1 and 1004-2, with sufficiently high operator-commanded propulsion 904. Also, in this example, system 100 modifies operator-commanded propulsion 904 even where operator-commanded propulsion 904 is quite small. In certain implementations, the modification of operator commanded-propulsion 904 are defined such that, for operator-commanded propulsion 904 typically encountered outside of the propulsion levels 1004-1 and 1004-2, manipulator cart propulsion 910-2 does not exceed these propulsion levels.

FIGS. 11A-11D further illustrate how exemplary operator-commanded propulsion 904 may be translated into manipulator cart propulsion 910 in accordance with different types of propulsion limitations 908. Specifically, each graph depicted in FIGS. 11A-11D depicts exemplary operator-commanded propulsion 904 along the x-axis, and depicts, along the y-axis, a corresponding manipulator cart propulsion 910 that results from one or more propulsion limitations 908 implemented by system 100. Accordingly, while not explicitly labeled in FIGS. 11A-11D, it will be understood that each graph is associated with a different propulsion limitation 908 (or a plurality thereof). It will also be understood that positive values (i.e., up and/or to the right) represent propulsion values such as speed or acceleration in the forward direction along path 404, while negative values (i.e., down and/or to the left) represent these propulsion values in the backward direction along path 404. Moreover, the dashed lines shown for each of the graphs in FIGS. 11A-11D will be understood to correspond to reference levels that are the same for both axes. Thus, for example, an operator-commanded speed at the vertical dashed line would translate to a manipulator cart speed at the horizontal dashed line if propulsion limitation 908 translated operator-commanded speed to manipulator cart speed in a one-to-one manner.

Figure 11A:
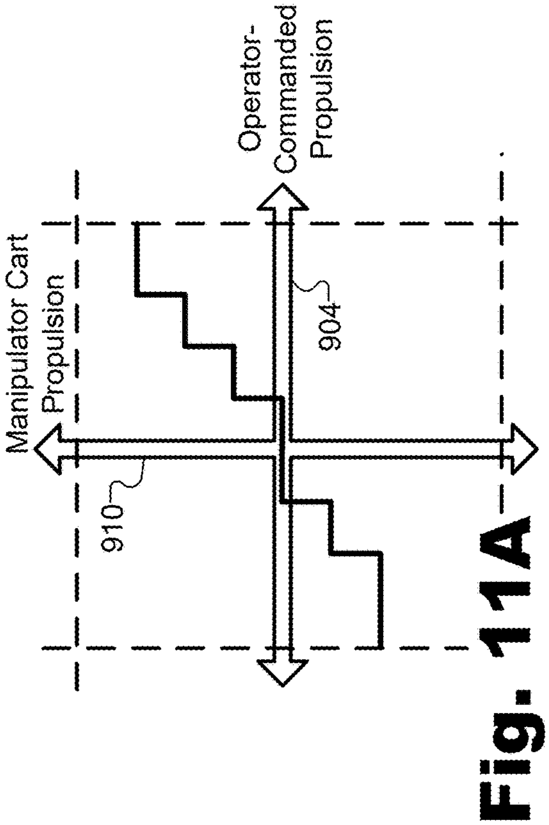
FIGS. 11A-11D illustrate how exemplary operator-commanded propulsion may be translated into manipulator cart propulsion in accordance with different types of propulsion limitations according to principles described herein.
Figure 12:
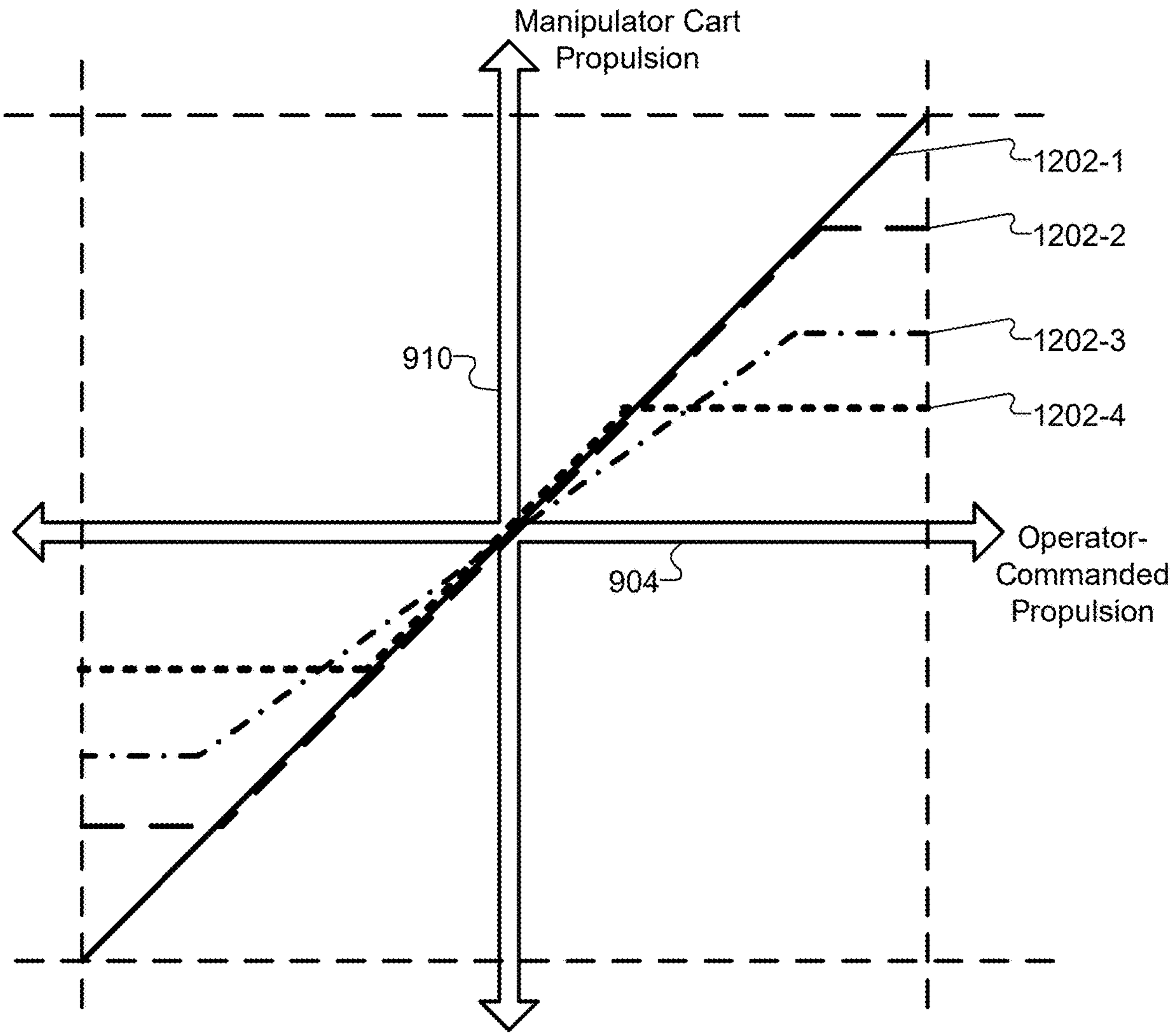
FIG. 12 illustrates how exemplary operator-commanded propulsion may be translated into manipulator cart propulsion in accordance with different types of propulsion limitations imposed in different zones or along different parts of a path according to principles described herein.

FIG. 11A shows an example where the propulsion limitation 908 limits operator-commanded propulsion 904 using a plurality of discrete propulsion limit levels. For example, as shown, three distinct propulsion levels (e.g., speed levels such as a low-speed level, an intermediate-speed level, and a high-speed level) are available in the forward direction, while two distinct propulsion levels (e.g., speed levels such as a low-speed level and a high-speed level) are available in the backward direction. In this example, each of the discrete propulsion values shown is applied only to operator-commanded propulsion values at or below that discrete propulsion value; thus, a higher operator-commanded propulsion value would encounter a higher propulsion limit level if such is available. Accordingly, as shown, an upper limit for forward speed may be implemented, as well as an upper limit for backward speed. As shown, the upper limit for forward speed is greater than the upper limit for backward speed in this example, although it will be understood that the reverse may be true or both upper speed limits (for forward and backward motion) may be equal in other examples.

Figure 11B:
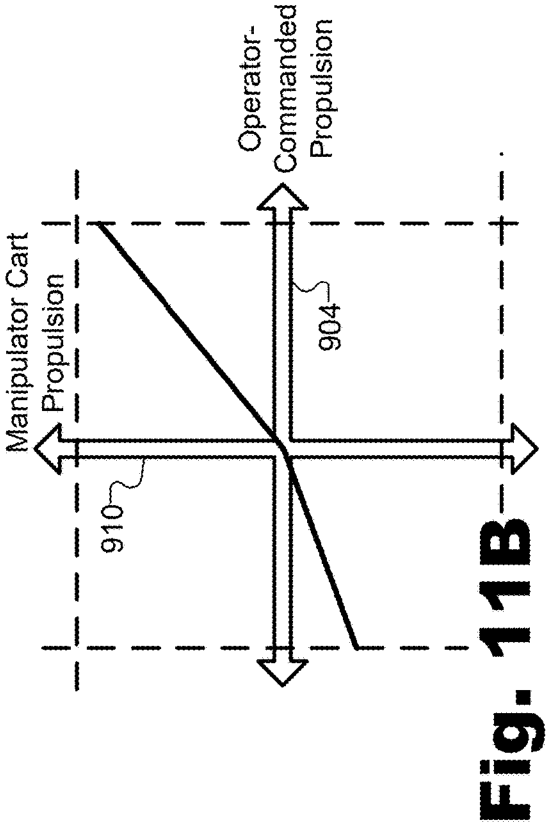

FIG. 11B shows an example where the propulsion limitation 908 translates operator-commanded propulsion 904 in a linear manner to a particular propulsion level on a continuum of propulsion levels. As shown, while the translation from operator-commanded propulsion 904 to manipulator cart propulsion 910 is linear, it is not unity. That is, the manipulator cart propulsion that is directed is a certain degree (e.g. about 90%) of any given operator-commanded propulsion. In this example, no upper limit is shown to be implemented. Rather, the propulsion commanded by operator 902 is simply reduced in the actual propulsion of manipulator cart 202. Another feature illustrated in FIG. 11B is that the mapping between operator-commanded propulsion 904 and manipulator cart propulsion 910 is different for the forward direction and the backward direction (i.e., manifested by different slopes in the top-right quadrant and the in the bottom left quadrant). In this way, the propulsion limitation 908 may compel operator 902 to move slowly (e.g., to slow down slightly) in the forward direction, and to move even more slowly (e.g., to slow down even more) in the backward direction. It will be understood that the slope of the lines in either of the quadrants may be any suitable slope, may be the same or different as one another, may change at certain propulsion levels, and so forth as may serve a particular implementation.

Figure 11C:
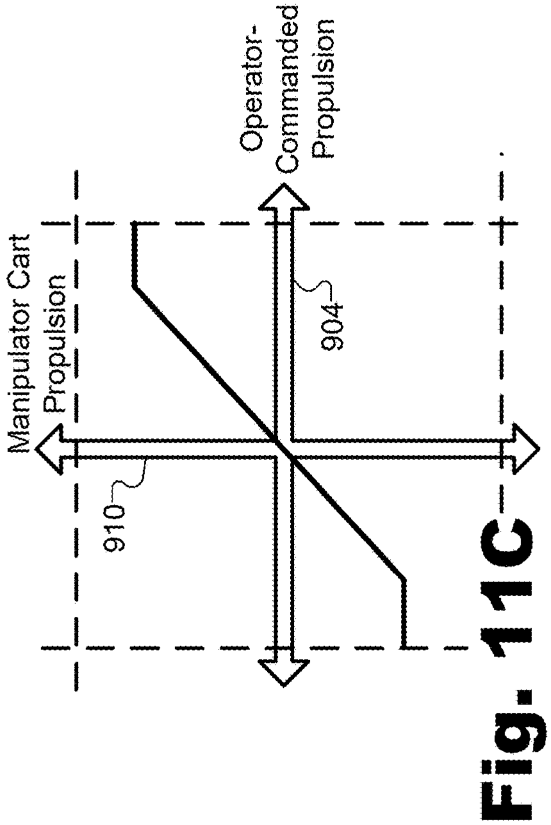

FIG. 11C shows another example in which a propulsion limitation 908 translates operator-commanded propulsion 904 in a linear manner to a particular propulsion level on a continuum of propulsion levels. While the example of FIG. 11C is similar to the example of FIG. 11B, the slope is now shown to be equal to 1 for both the forward and backward direction. Accordingly, in this example, the actual manipulator cart propulsion 910 that system 100 directs will be the same as the propulsion 904 that operator 902 commands, regardless of the direction along path 404. However, in contrast to the example of FIG. 11B, in this example, there are propulsion limitations (e.g., speed limits, acceleration limits, etc., depending on which characteristic is being represented) beyond which a higher operator-commanded propulsion value will not be translated to a higher manipulator cart propulsion value. These limits may be the same for both the forward and backward directions, or, as shown, in FIG. 11C, the limit for one direction may be higher than the limit for the other direction (i.e., the limit for the forward direction is shown to be slightly higher than the limit for the backward direction).

Figure 11D:
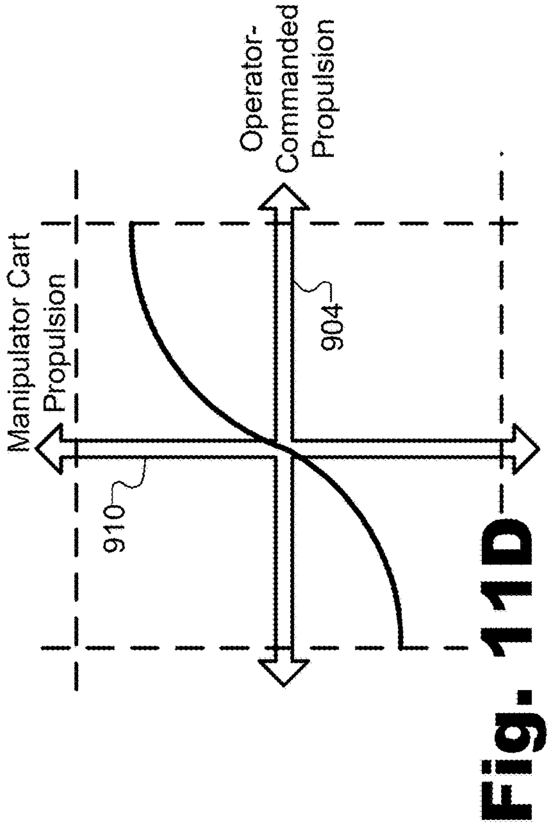

FIG. 11D shows another example in which a propulsion limitation 908 translates operator-commanded propulsion 904 to a particular propulsion level on a continuum of propulsion levels. In contrast to the linear nature of the translation in the examples of FIGS. 11B and 11C, the example of FIG. 11D shows that a non-linear translation may be used. As shown, upper limits such as speed limits, acceleration limits, or the like may still be implemented in this example. However, rather than being suddenly reached at particular value, these upper limits may be approached gradually (e.g., asymptotically). In this way, the propulsion control imposed by operator 902 does not saturate in such an abrupt way at a particular speed or acceleration, but, rather, additional increases in the commanded propulsion value have smaller and smaller impacts on the actual propulsion value as the propulsion value gets higher and manipulator cart 202 approaches the upper limit.

In some examples, it may be desirable for different propulsion limitations 908 to be used at different portions of path 404 or in different areas or zones of operating room 400. For instance, different types of propulsion limitations may be employed in different zones, different values for the propulsion limitations such as different speed gains (i.e., slopes in the graphs shown in FIGS. 11A-11D) may be used, and so forth. As one example, a relatively high speed gain may be designated for navigation of manipulator cart 202 through a high-speed zone (e.g., a portion of the path where there are no sharp curves, no nearby obstacles, and otherwise minimal risk). As another example, a relatively low speed gain may be designated for navigation of manipulator cart 202 through a low-speed zone (e.g., a portion of the path that has more difficult turns, obstacles on or near the path, and otherwise more significant risk than the high-speed zone).

To illustrate, FIG. 12 shows how exemplary operator-commanded propulsion 904 may be translated into manipulator cart propulsion 910 in accordance with different types of propulsion limitations 908 imposed in different zones or along different parts of path 404. Specifically, as shown, a plurality of plots 1202 (i.e., plots 1202-1 through 1202-4) that may each be associated with a different zone are shown on a graph similar to the graphs of FIGS. 11A-11D.

Plot 1202-1 (the solid line) is drawn with a slope of 1 and without any portion that levels off to represent an upper limit. Accordingly, plot 1202-1 may represent the translation that system 100 may perform in a high-speed zone in which there is little or no risk of manipulator cart 202 colliding with an obstacle, taking too sharp of a turn, or the like. As such, plot 1202-1 may represent behavior of system 100 when no propulsion limitation 908 is imposed.

Plot 1202-2 (the dashed line) is drawn with a slope of 1 along most of its length, but eventually levels off, representing an upper limit. Accordingly, plot 1202-2 may represent the translation that system 100 may perform in a relatively high-speed zone, but one in which there is an upper limit (e.g., due to a turning radius of manipulator cart 202 or the like).

Plot 1202-3 (the dash-dotted line) is drawn with a slope less than 1 and also eventually levels off to implement an upper limit. Accordingly, plot 1202-3 may represent the translation that system 100 may perform in a relatively low-speed zone where a lower speed gain and an maximum speed limit may both be appropriate (e.g., in order to avoid nearby obstacles, etc.)

Plot 1202-4 (the dotted line) also may be used for a relatively low-speed zone. In this example, however, the speed gain is shown to not be limited (i.e., such that the slope is 1), but there is an upper propulsion limit that is set at a relatively low value to ensure that operator 902 keeps the propulsion speed of manipulator cart 202 relatively low.

Propulsion limitations associated with any of plots 1202 or a variety of other plots that may serve a particular implementation may be implemented in various zones as may be appropriate. As mentioned above, a propulsion value such as a speed setting may be related to an exertion level that operator 902 applies to manipulator cart 202 (e.g., how hard operator 902 attempts to push or pull manipulator cart 202, how hard operator 902 engages a throttling mechanism for driving manipulator cart 202, etc.). As such, different propulsion limitations 908 associated with different plots 1202 may each include different mappings of the input exertion to a speed or an acceleration of manipulator cart 202. In some examples, operator 902 may haptically feel the difference between the different propulsion limitations 908 (e.g., when switching from one zone and one plot 1202 to another) based on how much exertion is required to achieve a desired speed or acceleration. For example, from the perspective of operator 902, manipulator cart 202 may seem lighter and faster to move when navigating a high-speed zone (e.g., when the propulsion limitation implements plot 1202-1 or 1202-2), and may feel heavier and slower to move when navigating a low-speed zone (e.g., when the propulsion limitation implements plot 1202-3).

Returning to FIG. 9, propulsion limitations 908 are shown to be imposed by system 100 based on one or more navigation conditions 906 that may be identified by system 100 in any of the ways described herein. Navigation conditions may be identified and mapped to any of the propulsion limitations described herein in any suitable way. For example, navigation conditions may be tracked by system 100, may be determined based on sensor data detected or accessed by system 100, may be indicated by input from another system or from operator input from operator 902, or may be identified in any other manner as may serve a particular implementation.

Navigation conditions 906 may relate to any of various conditions or circumstances associated with manipulator cart 202 or movable components included therein as a path is being navigated and a configuration plan is being carried out. For example, navigation conditions 906 may be relate to the path being navigated (e.g., path 404), a configuration plan for the movable components, obstacles along the path (e.g., obstacles 410 or 412), the initial and/or target locations of the path (e.g., locations 406-initial and/or 406-target), and/or any other aspect of the navigation of manipulator cart 202 along the path. Various non-limiting examples of navigation conditions 906 will now be described.

As one example, a navigation condition 906 identified by system 100 may be that manipulator cart 202 is navigating or approaching a turn along the path. The propulsion limitation 908 for such a navigation condition 906 may include a maximum speed limit (e.g., a maximum speed limit lower than a full speed achievable by the propulsion of manipulator cart 202) for when manipulator cart 202 is navigating the turn. As another example, a navigation condition 906 identified by system 100 may be that manipulator cart 202 is approaching an obstacle to be avoided by manipulator cart 202 during the navigation of manipulator cart 202 along the path, or is approaching the target location at the end of the path. In these examples, the propulsion limitation 908 may limit the speed as the obstacle or target location is approached. As yet another example, a navigation condition 906 identified by system 100 may be that manipulator cart 202 is navigating along a particular portion of the path (e.g., a portion within an area designated as a low-speed or high-speed zone, a portion within a sterile field, etc.) or is located in a particular area (e.g., an operating room versus a hallway in the hospital, etc.).

In certain implementations, manipulator cart propulsion 910 may be performed using battery power provided by a battery of manipulator cart 202. In such implementations, a navigation condition 906 identified by system 100 may be that manipulator cart propulsion 910 is performed using the battery power and/or that a battery level of the battery is below a predetermined battery level threshold. For example, propulsion limitations 908 limiting the speed or acceleration rate may be imposed in response to these types of navigation conditions if more battery power is consumed by higher speeds and/or acceleration rates than by lower speeds and/or acceleration rates. Similarly, in examples where manipulator cart 202 is connected to other objects by way of cables (e.g., power cables, communication cables, etc.), system 100 may track whether manipulator cart 202 is likely to begin pulling on a cable that is not long enough to allow manipulator cart 202 to navigate any further in a particular direction, and may impose propulsion limitations forcing manipulator cart 202 to slow or stop before any cable is pulled too hard (e.g., so as to come unplugged, undergo damage, or pose a safety risk such as a tripping hazard to people in the vicinity).

In some examples, a navigation condition 906 identified by system 100 may comprise an attention measurement indicative of attention paid to the navigation of manipulator cart 202 by a person in a vicinity of manipulator cart 202. For example, the person may be operator 902 and system 100 may detect (e.g., using gaze tracking techniques or the like) whether operator 902 is paying attention to certain aspects of the navigation (e.g., as opposed to directing his or her attention elsewhere while relying heavily on the ability of the system to automatically steer manipulator cart 202). If operator 902 is paying close attention, less significant propulsion limitations 908 may be required than if operator 902 appears to be distracted. As another example, the person may be a person in front of manipulator cart 202 on the path who is identified as a potential obstacle. If the person is detected to be paying attention and to be aware of manipulator cart 202 coming in his or her direction, less significant propulsion limitations may be necessary than if the person is detected to not have an awareness of the approach of manipulator cart 202 (e.g., if the person is detected to have his or her back turned to manipulator cart 202).

Other navigation conditions 906 that certain implementations of system 100 may identify relate to the overall entropy or chaos in the scene (e.g., in the operating room, etc.). For example, a navigation condition 906 may be that an entropy associated with the path is detected to satisfy a predetermined entropy criterion, and a propulsion limitation 908 such as a maximum speed limit or acceleration limit may be imposed on manipulator cart propulsion 910 until it is determined that the entropy is lower.

Figure 13:
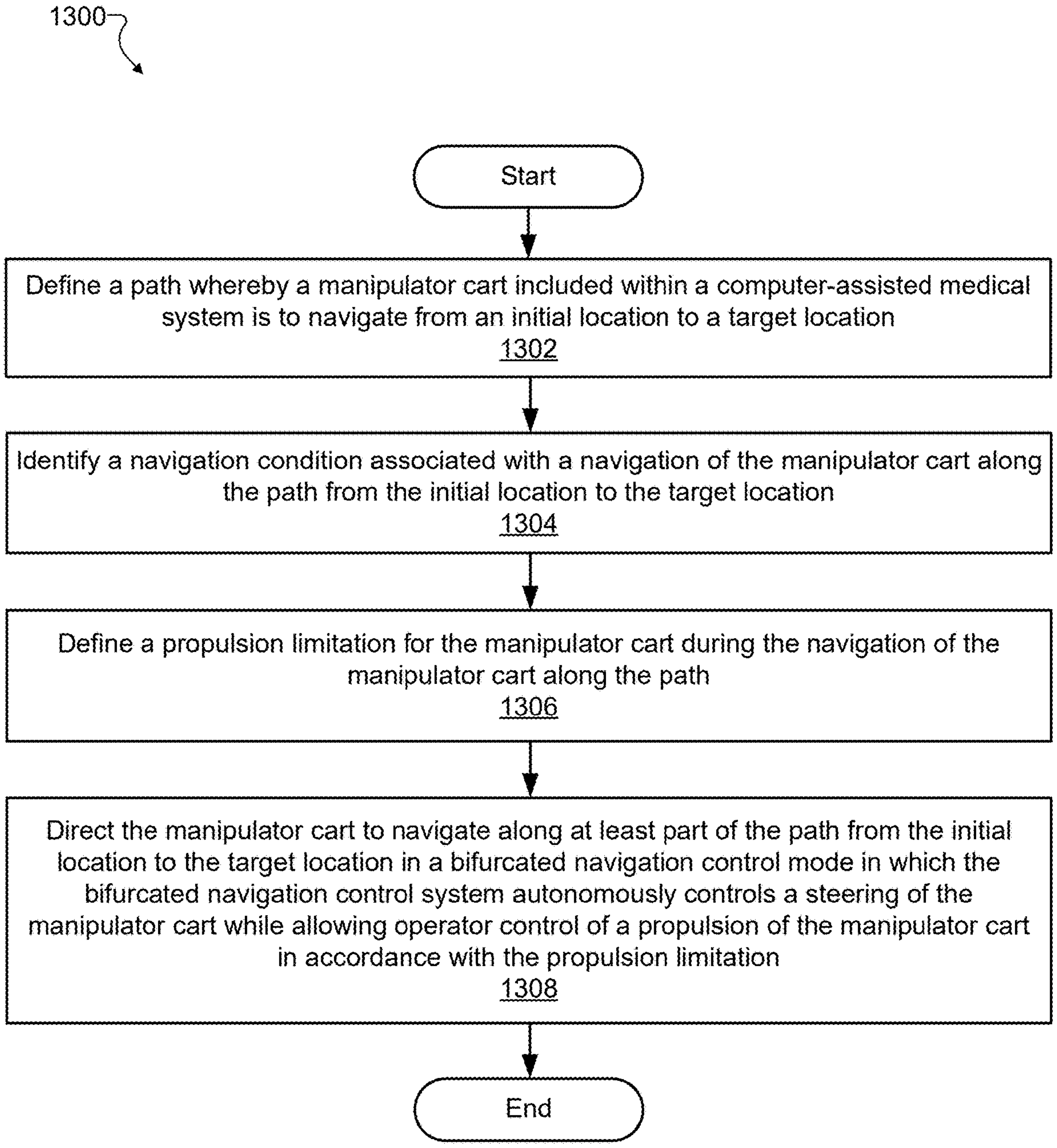
FIG. 13 illustrates an exemplary method for bifurcated navigation control of a manipulator cart included within a computer-assisted medical system according to principles described herein.

FIG. 13 illustrates an exemplary method 1300 for bifurcated navigation control of a manipulator cart included within a computer-assisted medical system. While FIG. 13 illustrates exemplary operations according to one embodiment, other embodiments may omit, add to, reorder, and/or modify any of the operations shown in FIG. 13. One or more of the operations shown in FIG. 13 may be performed by a bifurcated navigation control system such as system 100, any components included therein, and/or any implementation thereof.

In operation 1302, a bifurcated navigation control system may define a path whereby a manipulator cart included within a computer-assisted medical system is to navigate from an initial location to a target location. Operation 1302 may be performed in any of the ways described herein.

In operation 1304, the bifurcated navigation control system may identify a navigation condition associated with a navigation of the manipulator cart along the path from the initial location to the target location. Operation 1304 may be performed in any of the ways described herein.

In operation 1306, the bifurcated navigation control system may define a propulsion limitation for the manipulator cart during the navigation of the manipulator cart along the path. For example, the bifurcated navigation control system may define the propulsion limitation based on the navigation condition identified in operation 1304. Operation 1306 may be performed in any of the ways described herein.

In operation 1308, the bifurcated navigation control system may direct the manipulator cart to navigate along at least part of the path from the initial location to the target location. In particular, the bifurcated navigation control system may direct the manipulator cart to navigate in a bifurcated navigation control mode in which the bifurcated navigation control system autonomously controls a steering of the manipulator cart while allowing operator control of a propulsion of the manipulator cart in accordance with the propulsion limitation defined in operation 1306. Operation 1308 may be performed in any of the ways described herein.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

In some examples, any of the systems and/or other components described herein may be implemented by a computing device including one or more processors, storage devices, input/output modules, communication interfaces, buses, infrastructures, and so forth. For instance, storage facility 102 of system 100 may be implemented by a storage device of the computing device, and processing facility 104 of system 100 may be implemented by one or more processors of the computing device. In other examples, the systems and/or other components described herein may be implemented by any suitable non-transitory computer-readable medium storing instructions that, when executed, direct a processor of such a computing device to perform methods and operations described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:

a memory storing instructions; and a processor communicatively coupled to the memory, the processor configured to execute the instructions to:

identify a navigation condition associated with a navigation of a component of a computer-assisted medical system component along a path from an initial location to a target location;

determine, based on the navigation condition, a propulsion limitation configured to be imposed on operator-provided commands related to a propulsion of the component during the navigation of the component along the path; and direct the component to navigate, in a bifurcated navigation control mode, along at least part of the path from the initial location to the target location;

wherein, in the bifurcated navigation control mode, the processor is configured to execute the instructions to autonomously control a steering of the component while allowing operator control of the propulsion of the component based on the operator-provided commands as limited by the propulsion limitation.

2. The system of claim 1, wherein:

the initial location is associated with an initial orientation of the component;

the target location is associated with a target orientation of the component; and the processor is further configured to execute the instructions to define, with respect to the path, an orientation plan whereby the component is reoriented from the initial orientation to the target orientation.

3. The system of claim 1, wherein the propulsion limitation includes a maximum speed limit for the component.

4. The system of claim 3, wherein the processor is configured to define the maximum speed limit based on:

a proximity of the component to an obstacle to be avoided by the component during the navigation of the component along the path, and a predetermined deceleration rate of the component.

5. The system of claim 3, wherein:

the component comprises a movable component; and the processor is configured to define the maximum speed limit based on:

a proximity of the component to an obstacle to be avoided by the movable component during the navigation of the component along the path, an orientation of the movable component with respect to the obstacle, and a movement rate of the movable component.

6. The system of claim 1, wherein the propulsion limitation includes a maximum acceleration rate for the component.

7. The system of claim 1, wherein:

the propulsion limitation includes a designated speed gain associated with a speed control interface of the component; and in the bifurcated navigation control mode, the processor is configured to allow the operator control of the propulsion in accordance with the propulsion limitation by directing the propulsion of the component to be performed at a speed determined by:

an operator-selected speed setting for the speed control interface, and the designated speed gain associated with the speed control interface.

8. The system of claim 1, wherein:

the identified navigation condition is that the component is navigating or approaching a turn along the path; and the propulsion limitation includes a maximum speed limit for when the component is navigating the turn, the maximum speed limit lower than a full speed achievable by the propulsion of the component.

9. The system of claim 1, wherein the identified navigation condition is that the component is approaching an obstacle to be avoided by the component during the navigation of the component along the path.

10. The system of claim 9, wherein the determining the propulsion limitation for the component comprises:

determining a movability status or a risk factor of the obstacle; and accounting for the movability status or the risk factor of the obstacle.

11. The system of claim 1, wherein the identified navigation condition comprises at least one condition selected from the group consisting of:

a battery level of a battery used to power the propulsion of the component is below a predetermined battery level threshold;

an attention measurement indicative of attention paid to the navigation of the component by a person in a vicinity of the component; and an entropy associated with the path is detected to satisfy a predetermined entropy criterion.

12. The system of claim 1, wherein:

the initial location is associated with an initial configuration of a moveable component of the component;

the target location is associated with a target configuration of the moveable component of the component; and the processor is further configured to execute the instructions to define, with respect to the path, a configuration plan whereby the moveable component of the component is to transform from the initial configuration to the target configuration.

13. The system of claim 1, wherein the processor is further configured to execute the instructions to:

switch to a standard navigation control mode from the bifurcated navigation control mode, the standard navigation control mode allowing operator control of both the steering and the propulsion of the component.

14. The system of claim 13, wherein the switching to the standard navigation control mode from the bifurcated navigation control mode comprises:

transitioning, in response to operator input resisting autonomous steering of the component or an identified navigation condition, from directing the navigation along the path in the bifurcated navigation control mode to allowing navigation along the path in the standard navigation control mode.

15. The system of claim 1, wherein the path is defined to include at least one portion in which the component uses backward propulsion in order to progress along the path from the initial location to the target location.

16. A method comprising:

identifying, by a bifurcated navigation control system, a navigation condition associated with a navigation of a component of a computer-assisted medical system component along a path from an initial location to a target location;

determining, by the bifurcated navigation control system based on the navigation condition, a propulsion limitation configured to be imposed on operator-provided commands related to a propulsion of the component during the navigation of the component along the path; and directing, by the bifurcated navigation control system, the component to navigate, in a bifurcated navigation control mode, along at least part of the path from the initial location to the target location;

wherein, in the bifurcated navigation control mode, the bifurcated navigation control system autonomously controls a steering of the component while allowing operator control of the propulsion of the component based on the operator-provided commands as limited by the propulsion limitation.

17. The method of claim 16, wherein:

the initial location is associated with an initial orientation of the component;

the target location is associated with a target orientation of the component; and the method further comprises defining, with respect to the path, an orientation plan whereby the component is reoriented from the initial orientation to the target orientation.

18. The method of claim 16, wherein the propulsion limitation includes a maximum speed limit for the component.

19. The method of claim 16, wherein the identified navigation condition comprises at least one condition selected from the group consisting of:

a battery level of a battery used to power the propulsion of the component is below a predetermined battery level threshold;

an attention measurement indicative of attention paid to the navigation of the component by a person in a vicinity of the component; and an entropy associated with the path is detected to satisfy a predetermined entropy criterion.

20. A non-transitory computer-readable medium storing instructions that, when executed, direct a processor of a computing device to:

identify a navigation condition associated with a navigation of a component of a computer-assisted medical system component along a path from an initial location to a target location;

determine, based on the navigation condition, a propulsion limitation configured to be imposed on operator-provided commands related to a propulsion of the component during the navigation of the component along the path; and direct the component to navigate, in a bifurcated navigation control mode, along at least part of the path from the initial location to the target location;

wherein, in the bifurcated navigation control mode, the instructions direct the processor to autonomously control a steering of the component while allowing operator control of the propulsion of the component based on the operator-provided commands as limited by the propulsion limitation.

* * * * *